US011781103B2

(12) United States Patent
Taguchi

(10) Patent No.: US 11,781,103 B2
(45) Date of Patent: Oct. 10, 2023

(54) MICROORGANISM CONTAMINATION COUNTERMEASURE SELECTION DEVICE, MICROORGANISM CONTAMINATION COUNTERMEASURE SELECTION SYSTEM, MICROORGANISM CONTAMINATION COUNTERMEASURE SELECTION METHOD, AND NON-TRANSITORY COMPUTER READABLE STORAGE MEDIUM

(71) Applicant: Yokogawa Electric Corporation, Tokyo (JP)

(72) Inventor: Tomoyuki Taguchi, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 489 days.

(21) Appl. No.: 16/761,589

(22) PCT Filed: Nov. 10, 2017

(86) PCT No.: PCT/JP2017/040584
§ 371 (c)(1),
(2) Date: May 5, 2020

(87) PCT Pub. No.: WO2019/092847
PCT Pub. Date: May 16, 2019

(65) Prior Publication Data
US 2020/0270564 A1 Aug. 27, 2020

(51) Int. Cl.
*C12M 1/34* (2006.01)
*G16B 50/30* (2019.01)
(Continued)

(52) U.S. Cl.
CPC ............ *C12M 41/36* (2013.01); *C12M 41/48* (2013.01); *C12Q 1/04* (2013.01); *G16B 30/00* (2019.02); *G16B 50/30* (2019.02)

(58) Field of Classification Search
CPC ........ G16B 30/00; G16B 50/00; G16B 50/30; C12M 41/48; C12Q 1/004; C12Q 1/04
(Continued)

(56) References Cited

U.S. PATENT DOCUMENTS

| 2007/0172560 A1* | 7/2007 | Mirtsching | A23L 3/28 |
| | | | 426/325 |
| 2015/0125853 A1 | 5/2015 | Samadpour | |
| 2018/0105444 A1* | 4/2018 | Asako | C02F 3/006 |

FOREIGN PATENT DOCUMENTS

| EP | 1745139 B1 * | 6/2012 | ............... C12Q 1/04 |
| JP | 5565991 B2 | 8/2014 | |

(Continued)

OTHER PUBLICATIONS

Nakpan, Worrawit; Inactivation of Viable Stress-Resistant Microorganisms Using Novel Treatments; University of Cincinnati. ProQuest Dissertations Publishing, 2019. 13917685. (Year: 2019).*

*Primary Examiner* — Hiep V Nguyen
(74) *Attorney, Agent, or Firm* — Rankin, Hill & Clark LLP

(57) ABSTRACT

A microorganism contamination countermeasure selection device includes a gene information acquirer configured to acquire gene information indicating information on genes of microorganisms contained in a sample, an index determiner configured to determine at least one of microorganism indexes corresponding to the gene information acquired by the gene information acquirer based on the gene information acquired by the gene information acquirer and a microorganism index table in which a microorganism index based on features of the microorganisms is associated with at least one of the gene information, and a contamination countermeasure selector configured to select at least one of contamination countermeasures corresponding to the microorganism index determined by the index determiner based on (Continued)

the microorganism index determined by the index determiner and a contamination countermeasure table in which a contamination countermeasure against contamination by the microorganisms is associated with at least one of the microorganism indexes.

11 Claims, 11 Drawing Sheets

(51) Int. Cl.
*C12M 1/36* (2006.01)
*C12Q 1/04* (2006.01)
*G16B 30/00* (2019.01)

(58) Field of Classification Search
USPC .......................................................... 705/2
See application file for complete search history.

(56) References Cited

FOREIGN PATENT DOCUMENTS

JP          2016-197331  A      11/2016
WO      WO-2019092847 A1 *   5/2019   .............. C12M 1/00

* cited by examiner

FIG. 8

| NUCLEOTIDE SEQUENCE | 2031 |
|---|---|
| NUCLEOTIDE SEQUENCE 1 | |
| NUCLEOTIDE SEQUENCE 2 | |
| NUCLEOTIDE SEQUENCE 3 | |
| NUCLEOTIDE SEQUENCE 4 | |
| NUCLEOTIDE SEQUENCE 5 | |
| NUCLEOTIDE SEQUENCE 6 | |
| NUCLEOTIDE SEQUENCE 7 | |
| NUCLEOTIDE SEQUENCE 8 | |
| NUCLEOTIDE SEQUENCE 9 | |
| ⋮ | |
| NUCLEOTIDE SEQUENCE M | |
| NUCLEOTIDE SEQUENCE M+1 | |
| NUCLEOTIDE SEQUENCE M+2 | |

FIG. 9

| MICROORGANISM INDEX | NUCLEOTIDE SEQUENCE | 1131 |
|---|---|---|
| CATEGORY 1 | NUCLEOTIDE SEQUENCE 1 | |
| CATEGORY 1 | NUCLEOTIDE SEQUENCE 2 | |
| CATEGORY 1 | NUCLEOTIDE SEQUENCE 3 | |
| CATEGORY 1 | NUCLEOTIDE SEQUENCE 4 | |
| CATEGORY 2 | NUCLEOTIDE SEQUENCE 5 | |
| CATEGORY 2 | NUCLEOTIDE SEQUENCE 6 | |
| CATEGORY 3 | NUCLEOTIDE SEQUENCE 7 | |
| CATEGORY 3 | NUCLEOTIDE SEQUENCE 8 | |
| CATEGORY 3 | NUCLEOTIDE SEQUENCE 9 | |
| ⋮ | ⋮ | |
| CATEGORY N | NUCLEOTIDE SEQUENCE M | |
| CATEGORY N | NUCLEOTIDE SEQUENCE M+1 | |
| CATEGORY N | NUCLEOTIDE SEQUENCE M+2 | |

FIG. 10

| 1251 | COUNTER-MEASURE 1 (DISCARDING LOTS) | COUNTER-MEASURE 2 (SAMPLING DISCARDING) | COUNTER-MEASURE 3 (CIP CLEANING) | COUNTER-MEASURE 4 (SIP STERI-LIZATION) | COUNTER-MEASURE 5 (DISASSEMBLING AND CLEANING PRODUCTION LINES) | ... | COUNTER-MEASURE L (CHANGE RAW MATERIALS) |
|---|---|---|---|---|---|---|---|
| CATEGORY 1 (HUMAN RESIDENT) | △ | ○ | △ | △ | △ | ... | × |
| CATEGORY 2 (HEAT-RESISTANT) | ○ | ○ | ○ | ○ | ○ | ... | ○ |
| CATEGORY 3 (ACID-RESISTANT) | ○ | ○ | ○ | ○ | △ | ... | ○ |
| CATEGORY 4 (ALKALINE-RESISTANT) | ○ | ○ | ○ | △ | △ | ... | ○ |
| CATEGORY 5 (PERACETIC ACID-RESISTANT) | ○ | ○ | ○ | △ | ○ | ... | ○ |
| CATEGORY 6 (HYDROGEN PEROXIDE-RESISTANT) | ○ | △ | △ | △ | ○ | ... | △ |
| CATEGORY 7 (BIOFILM FORMING) | ○ | ○ | ○ | △ | ○ | ... | ○ |
| CATEGORY 8 (CHEMICAL-RESISTANT) | ○ | △ | △ | △ | ○ | ... | △ |
| CATEGORY 9 (SPORE-FORMING) | ○ | × | ○ | ○ | ○ | ... | ○ |
| CATEGORY 10 (TOXIN-PRODUCING) | ... | ... | ... | ... | ... | ... | ... |
| CATEGORY N (CHLORINE-RESISTANT) | ○ | ○ | ○ | △ | ○ | ... | ○ |

FIG. 11

| SAMPLE INFORMATION |
| --- |
| SAMPLING DATE/TIME |
| SAMPLING AMOUNT |
| SAMPLING METHOD |
| OPERATOR |
| INSPECTION LOT |
| INSPECTION METHOD |
| INSPECTION REAGENT LOT |
| ⋮ |

FIG. 12

| PRODUCTION INFORMATION |
| --- |
| PROCESSING TEMPERATURE |
| INTERMEDIATE INSPECTION RESULT |
| PRODUCTION LINE |
| PROCESSING DATE |
| PREPARATION DATE |
| PROCESSING START TIME |
| PROCESSING END TIME |
| OPERATOR |
| PRODUCTION ENVIRONMENT INSPECTION RESULT |
| STERILIZATION TEMPERATURE |
| STERILIZATION METHOD |
| PRODUCTION LOT |
| PRODUCTION WATER INSPECTION RESULT |
| APPEARANCE INSPECTION RESULT |
| SENSORY INSPECTION RESULT |
| ⋮ |

FIG. 13

| RAW MATERIAL INFORMATION |
|---|
| PRODUCTION AREA |
| PROCESSING AREA |
| PROCESSING DATE |
| EXPIRATION DATE |
| LOT NUMBER |
| STORAGE CONDITIONS |
| STORAGE STATUS |
| INSPECTION HISTORY |
| PRODUCT TYPE |
| DELIVERY SPECIFICATIONS |
| DELIVERY DATE |
| ACCEPTANCE INSPECTION RESULT |
| ⋮ |

FIG. 14

| PRODUCTION INFORMATION STATISTICAL DATA | ~4031 |
|---|---|
| PROCESSING TEMPERATURE | |
| INTERMEDIATE INSPECTION RESULT | |
| PRODUCTION LINE | |
| PROCESSING DATE | |
| PREPARATION DATE | |
| PROCESSING START TIME | |
| PROCESSING END TIME | |
| OPERATOR | |
| PRODUCTION ENVIRONMENT INSPECTION RESULT | |
| STERILIZATION TEMPERATURE | |
| STERILIZATION METHOD | |
| PRODUCTION LOT | |
| PRODUCTION WATER INSPECTION RESULT | |
| APPEARANCE INSPECTION RESULT | |
| SENSORY INSPECTION RESULT | |
| ⋮ | |

FIG. 15

| RAW MATERIAL INFORMATION STATISTICAL DATA | ~4032 |
|---|---|
| PRODUCTION AREA | |
| PROCESSING AREA | |
| PROCESSING DATE | |
| EXPIRATION DATE | |
| LOT NUMBER | |
| STORAGE CONDITIONS | |
| STORAGE STATUS | |
| INSPECTION HISTORY | |
| PRODUCT TYPE | |
| DELIVERY SPECIFICATIONS | |
| DELIVERY DATE | |
| ⋮ | |

FIG. 16

| FOLLOW-UP COUNTERMEASURE DATA | ~4034 |
|---|---|
| DISCARDING LOTS | |
| SAMPLING DISCARDING | |
| CIP CLEANING | |
| SIP STERILIZATION | |
| DISASSEMBLING AND CLEANING PRODUCTION LINES | |
| OPERATOR HYGIENE MANAGEMENT | |
| DISCARDING (REMAINING) RAW MATERIALS | |
| ALERTING OTHER FACTORIES | |
| CHANGE STERILIZATION CONDITIONS | |
| CHANGE STERILIZATION METHOD | |
| CHANGE CLEANING AGENT | |
| ⋮ | |
| CHANGE RAW MATERIALS | |

MICROORGANISM CONTAMINATION COUNTERMEASURE SELECTION DEVICE, MICROORGANISM CONTAMINATION COUNTERMEASURE SELECTION SYSTEM, MICROORGANISM CONTAMINATION COUNTERMEASURE SELECTION METHOD, AND NON-TRANSITORY COMPUTER READABLE STORAGE MEDIUM

TECHNICAL FIELD

The present invention relates to a microorganism contamination countermeasure selection device, a microorganism contamination countermeasure selection system, a microorganism contamination countermeasure selection method, and a non-transitory computer readable storage medium.

BACKGROUND ART

In recent years, due to stringent food safety requirements, it has become urgent for processed food manufacturers to improve a product production yield, reduce inspection costs, and provide safe and secure food without contamination of foreign substances. In departments responsible for the quality assurance of processed food manufacturers, there is a need not only for inspection for foreign substances in final products but also to quickly inspect intermediate products generated in production processes and feed back to the production process and return information for improvement.

Among foreign substance inspections, microorganism contamination inspection in which visual inspection is not possible, and there is no immediate detection technique such as a metal detector is one of inspections for quality assurance work for processed food which is a greatest bottleneck.

A microorganism contamination inspection is a task of detecting microorganisms contaminating an intermediate product sampled by an inspector, a sample obtained by wiping production lines, and a sampled final product and identifying the amount of contamination and a microorganism species.

Examples of a conventional main method of inspecting for microorganism contamination include a culture method. In this culture method, a medium in which microorganisms to be inspected for can grow is appropriately used. The inspector inoculates the sample into this medium, incubates the medium at a temperature at which subject microorganisms can grow, allows the microorganisms to grow, and determine microorganism contaminations, for example, visually.

The medium used here is generally a medium with a composition for a wide culture range because the contaminating microorganisms cannot be determined before inspection. In the case of a solid phase culture including agar or the like, although it may be possible to infer the species of contaminating microorganisms based on the color, texture, shape or the like of the resulting colonies, it is difficult to identify contaminating microorganisms simply by culturing using such as medium.

Therefore, when contaminating microorganisms are detected, re-culturing using a medium additionally containing a specific component for identifying microorganisms called a selection medium is performed and the species of microorganisms is identified.

In addition, in addition to a method of identifying the species of microorganisms according to a culture method using this selection medium, a method of identifying the species of microorganisms by inspecting biochemical reactions and a method of identifying the species of microorganisms by extracting nucleic acids from grown microorganisms and analyzing the nucleic acid sequence are used. For example, in a microorganism species determination system described in Patent Document 1, homology searching is performed using a database that includes sequence data of genes with high conservation in microorganisms and a database that includes the classification relationship between microorganisms, and determination of the species of microorganism is performed with higher accuracy.

Contaminating microorganisms may be identified by the above microorganism species identifying methods, and countermeasures taken based on previous knowledge of the identified microorganisms when microorganism contamination accidents occur.

CITATION LIST

Patent Literature

[Patent Literature 1]
Japanese Patent No. 5565991

In a microorganism identifying method according to a conventional culture method, an inspector needs to select a selection medium for identifying microorganisms although the type of contaminating microorganisms is unknown. The selection medium can generally only determine whether there is a certain specific microorganism. Therefore, in order to identify contaminating microorganisms, since it is necessary to repeat culture using different types of selection media, there is a problem of an inspection time and the inspection costs increasing.

In addition, in an identifying method using biochemical reactions, as described above, it is necessary to repeat different biochemical reactions, and thus the same problems occur. In addition, even if nucleic acids are inspection subjects, in a method based on a PCR method, similar problems that selection of different primers needs to be repeated occur.

On the other hand, in a method using a DNA sequencing technology for analyzing specific gene sequences, the problem of the above test being repeated does not occur, but there is a problem of significantly high inspection costs.

In addition, in an identifying method using a selection medium, microorganisms are identified from indexes such as the shape, color, and texture of the resulting microorganism colonies. Therefore, there are problems that an inspector with experience in colony identification is required and an inspector without skills or experience cannot easily identify microorganisms.

As described above, when the species of contaminating microorganisms is identified and a follow-up countermeasure is selected, there are problems that the inspection time and inspection costs are high and an inspector with expertise is necessary.

The present invention has been made in view of the above problems, and an object of the present invention is to provide a microorganism contamination countermeasure selection device, a microorganism contamination countermeasure selection system, a microorganism contamination countermeasure selection method, and a microorganism contamination countermeasure selection program through which the species of contaminating microorganisms is not identified such that an inspection time and the inspection costs can be reduced, and an appropriate follow-up countermeasure can be selected without the need for an inspector with expertise.

SUMMARY OF INVENTION

Solution to Problem

The present invention has been made in order to solve the above problems, one aspect of the present invention providing a microorganism contamination countermeasure selection device including a gene information acquirer configured to acquire gene information indicating information on genes of microorganisms contained in a sample, an index determiner configured to determine at least one of microorganism indexes corresponding to the gene information acquired by the gene information acquirer based on the gene information acquired by the gene information acquirer and a microorganism index table in which a microorganism index based on features of the microorganisms is associated with at least one of the gene information, and a contamination countermeasure selector configured to select at least one of contamination countermeasures corresponding to the microorganism index determined by the index determiner based on the microorganism index determined by the index determiner and a contamination countermeasure table in which a contamination countermeasure against contamination by the microorganisms is associated with at least one of the microorganism indexes.

In addition, in one aspect of the present invention, the microorganism contamination countermeasure selection device further includes a product information acquirer configured to acquire product information on a product from which the sample is collected, and the contamination countermeasure selector selects the contamination countermeasure based on the product information.

In addition, in one aspect of the present invention, in the microorganism contamination countermeasure selection device, the product information includes at least one of a type of the product, a production time of the product, a sterilization treatment performed on the product and raw materials of the product.

In addition, in one aspect of the present invention, the microorganism contamination countermeasure selection device further includes a statistical information acquirer configured to acquire statistical information including at least one of product information used in past contamination countermeasure selection and past contamination countermeasure implementation cases, and the contamination countermeasure selector selects the contamination countermeasure based on the statistical information.

In addition, in one aspect of the present invention, in the microorganism contamination countermeasure selection device, the gene information is information indicating nucleotide sequences of the microorganisms.

In addition, one aspect of the present invention provides a microorganism contamination countermeasure selection system including a gene analyzer configured to generate gene information based on analysis results of genes of microorganisms contained in a sample, an index determiner configured to determine at least one of a microorganism index corresponding to the gene information generated by the gene analyzer based on the gene information generated by the gene analyzer and a microorganism index table in which a microorganism index based on features of the microorganisms is associated with at least one of the gene information, and a contamination countermeasure selector configured to select at least one of contamination countermeasures corresponding to the microorganism index determined by the index determiner based on the microorganism index determined by the index determiner and a contamination countermeasure table in which a contamination countermeasure against contamination by the microorganisms is associated with at least one of the microorganism indexes.

In addition, in one aspect of the present invention, the microorganism contamination countermeasure selection system further includes a product information inputter configured to receive an input of product information on a product from which the sample is collected, and the contamination countermeasure selector selects the contamination countermeasure based on the product information.

In addition, in one aspect of the present invention, the microorganism contamination countermeasure selection system further includes a statistical information storage configured to store statistical information including at least one of product information used in past contamination countermeasure selection and past contamination countermeasure implementation cases, and the contamination countermeasure selector selects the contamination countermeasure based on the statistical information.

In addition, one aspect of the present invention provides a microorganism contamination countermeasure selection method performed by a computer, including a gene information acquisition step in which gene information indicating information on genes of microorganisms contained in a sample is acquired, an index determination step in which at least one of microorganism indexes corresponding to the gene information acquired in the gene information acquisition step is determined based on the gene information acquired in the gene information acquisition step and a microorganism index table in which a microorganism index based on features of the microorganisms is associated with at least one of the gene information, and a contamination countermeasure selection step in which at least one of contamination countermeasures corresponding to the microorganism index determined in the index determination step is selected based on the microorganism index determined in the index determination step and a contamination countermeasure table in which a contamination countermeasure against contamination by the microorganisms is associated with at least one of the microorganism indexes.

In addition, one aspect of the present invention provides a microorganism contamination countermeasure selection program causing a computer to execute: a gene information acquisition step in which gene information indicating information on genes of microorganisms contained in a sample is acquired, an index determination step in which at least one of microorganism indexes corresponding to the gene information acquired in the gene information acquisition step is determined based on the gene information acquired in the gene information acquisition step and a microorganism index table in which a microorganism index based on features of the microorganisms is associated with at least one of the gene information, and a contamination countermeasure selection step in which at least one of contamination countermeasures corresponding to the microorganism index determined in the index determination step is selected based on the microorganism index determined in the index determination step and a contamination countermeasure table in which a contamination countermeasure against contamination by the microorganisms is associated with at least one of the microorganism indexes.

According to the present invention, it is possible to select an appropriate follow-up countermeasure without identifying the species of contaminating microorganisms.

BRIEF DESCRIPTION OF DRAWINGS

FIG. 8 is a diagram showing a configuration of a gene information list stored in the gene analyzing device according to one embodiment of the present invention.

FIG. 9 is a diagram showing a configuration of a microorganism index table stored in the microorganism contamination countermeasure selection device according to one embodiment of the present invention.

FIG. 10 is a diagram showing a configuration of a contamination countermeasure table stored in the microorganism contamination countermeasure selection device according to one embodiment of the present invention.

FIG. 11 is a diagram showing a configuration of sample information input to the product information input device according to one embodiment of the present invention.

FIG. 12 is a diagram showing a configuration of production information input to the product information input device according to one embodiment of the present invention.

FIG. 13 is a diagram showing a configuration of raw material information input to the product information input device according to one embodiment of the present invention.

FIG. 14 is a diagram showing a configuration of production information statistical data stored in the statistical information database server according to one embodiment of the present invention.

FIG. 15 is a diagram showing a configuration of raw material information statistical data stored in the statistical information database server according to one embodiment of the present invention.

FIG. 16 is a diagram showing a configuration of follow-up countermeasure data stored in the statistical information database server according to one embodiment of the present invention.

DESCRIPTION OF EMBODIMENTS

Figure 1:
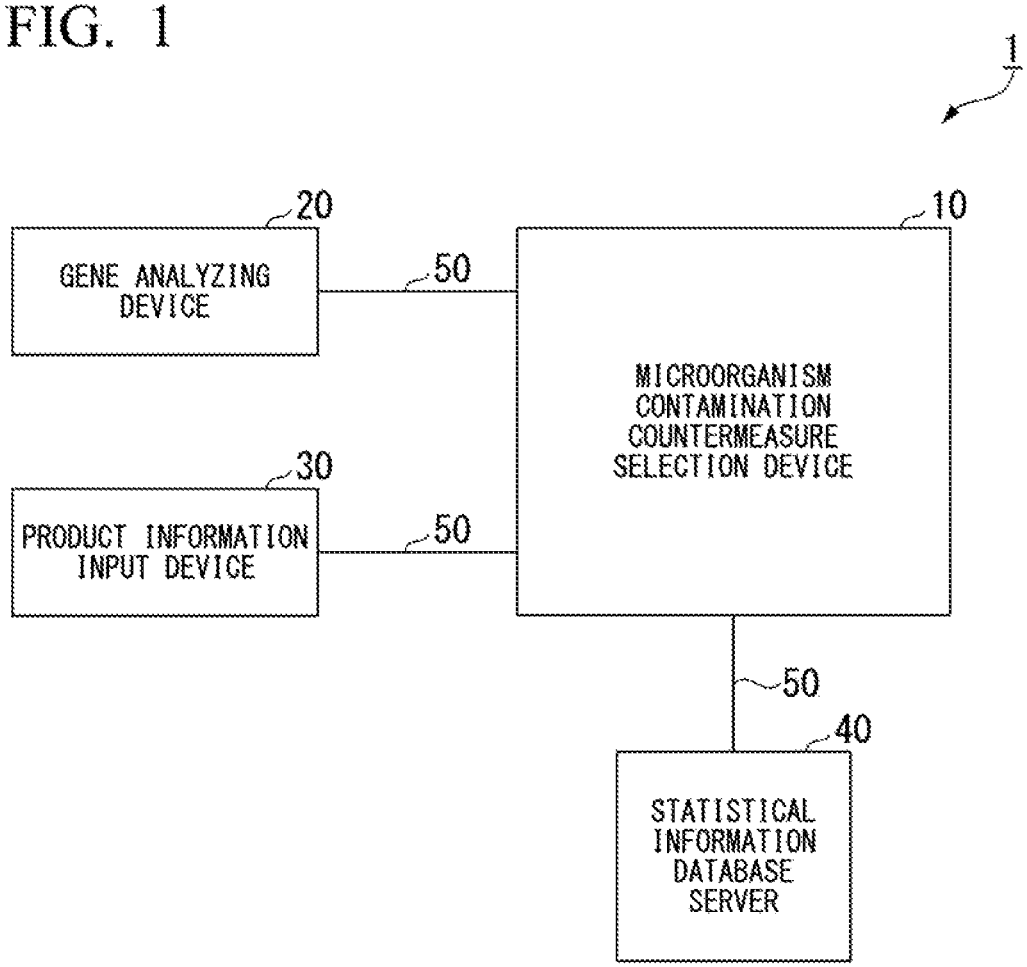
FIG. 1 is a schematic diagram showing an overview of a configuration of a microorganism contamination countermeasure selection system according to one embodiment of the present invention.

Hereinafter, the present invention will be described with reference to embodiments of the invention, but the embodiments described below do not limit the inventions according to the scope of the claims. In addition, not all combinations of features described in the following embodiments are necessarily essential as units as a solution for the invention. Here, in the drawings, the same or similar parts will be denoted with the same reference numerals and redundant descriptions may be omitted. In addition, shapes and sizes of elements in the drawings may be exaggerated for clearer description.

<Embodiments>

Hereinafter, embodiments of the present invention will be described. A microorganism contamination countermeasure selection system according to the present embodiment described below includes a sample analysis unit configured to acquire properties (features) of contaminating microorganisms, a unit for classifying contaminating microorganisms as a contaminating microorganism classification linked to a countermeasure (contamination countermeasure) for contaminating microorganisms, and a contamination countermeasure database.

[Configuration of Microorganism Contamination Countermeasure Selection System]

Hereinafter, the configuration of a microorganism contamination countermeasure selection system 1 will be described with reference to the drawings.

FIG. 1 is a schematic diagram showing an overview of a configuration of the microorganism contamination countermeasure selection system 1 according to one embodiment of the present invention.

The microorganism contamination countermeasure selection system 1 according to the present embodiment is, for example, an information processing system that is used by staff (hereinafter collectively referred to as a "user") in departments responsible for quality assurance of processed food manufacturers in order to select a countermeasure when a product is contaminated with microorganisms or the like.

Here, the microorganism contamination countermeasure selection system 1 according to the present embodiment can be used for selecting a countermeasure against contamination by microorganisms not only in foods and beverages but also in products (for example, pharmaceuticals or cosmetics) in other commercial fields.

As shown in FIG. 1, the microorganism contamination countermeasure selection system 1 includes a microorganism contamination countermeasure selection device 10, a gene analyzing device 20, a product information input device 30, a statistical information database server 40, and a communication network 50.

The microorganism contamination countermeasure selection device 10 acquires information (gene information) on nucleotide sequences of microorganisms contained in the sample collected from the product from the gene analyzing device 20. The microorganism contamination countermeasure selection device 10 stores in advance a microorganism index table in which a microorganism index based on features of microorganisms is associated with at least one nucleotide sequence. Based on the nucleotide sequence and microorganism index table on the basis of the acquired gene information, the microorganism contamination countermeasure selection device 10 determines at least one microorganism index corresponding to a nucleotide sequence based on the acquired gene information.

The microorganism index is data representing the type (category) of microorganisms. Here, examples of the microorganism index include "human resident microorganisms," "heat-resistant microorganisms," "acid-resistant microorganisms," "alkaline-resistant microorganisms," "peracetic acid-resistant microorganisms," "hydrogen peroxide-resistant microorganisms," "biofilm forming microorganisms," "chemical-resistant microorganisms," "spore-forming microorganisms," "toxin-producing microorganisms," "dry-resistant microorganisms," "water-resistant microorganisms," "hygrophilic microorganisms," "xerophilic microorganisms," "oligotrophic proliferative microorganisms," "slow proliferative microorganisms," "acidophilic microorganisms," "alkaliphilic microorganisms," "germ-forming microorganisms," "bacteria," "fungi," "protozoa," "viruses," "low temperature proliferative microorganisms," "cold-resistant microorganisms," "radiation-resistant microorganisms," "electron-resistant microorganisms," "gamma ray-resistant microorganisms," "ethylene oxide gas (EOG)-resistant microorganisms," "UV-resistant microorganisms," "surfactant-resistant microorganisms," "phenol-resistant microorganisms," "alcohol-resistant microorganisms," "anaerobic microorganisms," "aerobic microorganisms," "gram-positive microorganisms," "gram-negative microorganisms," "sulfate-reducing microorganisms," and "chlorine-resistant microorganisms."

In addition, the microorganism contamination countermeasure selection device 10 stores in advance a contamination countermeasure table in which a contamination countermeasure against contamination by microorganisms is associated with at least one microorganism index. The microorganism contamination countermeasure selection device 10 selects at least one of contamination countermeasures corresponding to each of the determined microorganism indexes based on the determined microorganism index and the contamination countermeasure table. The microorganism contamination countermeasure selection device 10 outputs information indicating the selected contamination countermeasure to the user.

Here, examples of contamination countermeasures include "discarding lots," "sampling discarding," "cleaning in place (CIP)," "sterilizing in place (SIP)," "disassembling and cleaning production lines," "hygiene management for operator," "discarding (remaining) raw materials," "alerting other factories," "change sterilization conditions," "change sterilization method," "change cleaning agent," and "change raw materials."

Here, the microorganism contamination countermeasure selection device 10 not only selects a contamination countermeasure based on the determined microorganism index and the contamination countermeasure table but also can further narrow down the selected contamination countermeasures using product information acquired from the product information input device 30. Here, details of product information and a process of narrowing down contamination countermeasures using the product information will be described below in detail. In addition, the microorganism contamination countermeasure selection device 10 can further narrow down the selected contamination countermeasures using statistical information acquired from the statistical information database server 40. Here, details of the statistical information and a process of narrowing down contamination countermeasures using the statistical information will be described below in detail.

The microorganism contamination countermeasure selection device 10 includes an information processing device, for example, a general-purpose computer or a personal computer.

In addition, the microorganism contamination countermeasure selection device 10 is connected to communicate with the gene analyzing device 20, the product information input device 30, and the statistical information database server via the communication network 50, and can transmit and receive data.

The communication network 50 is composed of, for example, the Internet, various closed networks (for example, a dedicated line, and a virtual private network (VPN)), or a combination of these communication networks. Here, the communication network 50 may be a communication network for wired communication or a part or all thereof may be a communication network for wireless communication.

Here, examples of communication networks for wireless communication here include communication networks according to wireless communication standards such as Wi-Fi (registered trademark) (Wireless-Fidelity), 3G (3rd Generation; third generation mobile communication system)/LTE (registered trademark) (Long Term Evolution), WiMAX (registered trademark) (Worldwide Interoperability for Microwave Access), and Bluetooth (registered trademark).

Here, the communication network 50 may be a communication network for wireless communication or wired communication based on other communication standards.

The gene analyzing device 20 detects microorganisms contained in the sample collected from the product and detects genes (nucleotide sequence) of the detected microorganisms. The gene analyzing device 20 stores in advance a list of nucleotide sequences of target microorganisms (gene information list). The gene analyzing device 20 performs an analysis for comparing the detected nucleotide sequences with nucleotide sequences included in the gene information list, and extracts a matching nucleotide sequence.

The gene analyzing device 20 generates information (gene information) indicating nucleotide sequences of the microorganisms, which is an analysis result of microorganisms contained in the sample collected from the product. The gene analyzing device 20 outputs the generated gene information to the microorganism contamination countermeasure selection device 10 via the communication network 50.

The gene analyzing device 20 includes a detection device that detects genes (nucleotide sequence) of microorganisms from the microorganisms contained in the sample collected from the product, for example, a cartridge or a reading device including a microarray (DNA (deoxyribonucleic acid) chip), and an information processing device that analyzes the detected nucleotide sequence, for example, a dedicated computer, and a personal computer.

For example, when the user sets the sample collected from the product on a microarray, detection of microorganisms contained in the sample and detection and analysis of genes (nucleotide sequence) of the detected microorganisms start.

Here, the gene analyzing device 20 may have a configuration different from the above configuration as long as it has a function of detecting a specific nucleotide sequence. For example, a configuration in which sequence analysis or another detection technique is used may be used in place of using a method using a microarray.

The product information input device 30 receives an input of product information based on an operation input by a user and outputs the input product information to the microorganism contamination countermeasure selection device 10 via the communication network 50.

The product information referred to here is product information on a product from which a sample is collected. The product information includes sample information which is information on a sample or sampling of the sample, production information which is information on a product from which a sample is collected or production of the product, and raw material information which is information on raw materials used in a product from which a sample is collected.

The product information input device 30 includes an information processing device, for example, a general-purpose computer, a personal computer, a tablet type small information terminal, or a smartphone.

The statistical information database server 40 stores in advance various types of statistical information on contamination countermeasures. The statistical information database server 40 appropriately extracts statistical information used for selecting a contamination countermeasure by the microorganism contamination countermeasure selection device 10 from among various types of statistical information stored in advance based on an acquisition request from the microorganism contamination countermeasure selection device 10. The statistical information database server 40 outputs the extracted statistical information to the microorganism contamination countermeasure selection device 10 via the communication network 50.

The statistical information referred to here includes production information statistical data and raw material information statistical data which are statistical data of product information used in past contamination countermeasure selection, past case data indicating past contamination countermeasure implementation cases (past cases), and follow-up countermeasure data indicating follow-up countermeasures implemented in past contamination countermeasure implementation cases.

The statistical information database server 40 includes an information processing device, for example, a general-purpose computer or a personal computer.

[Configuration of Microorganism Contamination Countermeasure Selection Device]

Hereinafter, the configuration of the microorganism contamination countermeasure selection device 10 will be described in more detail with reference to the drawings.

Figure 2:
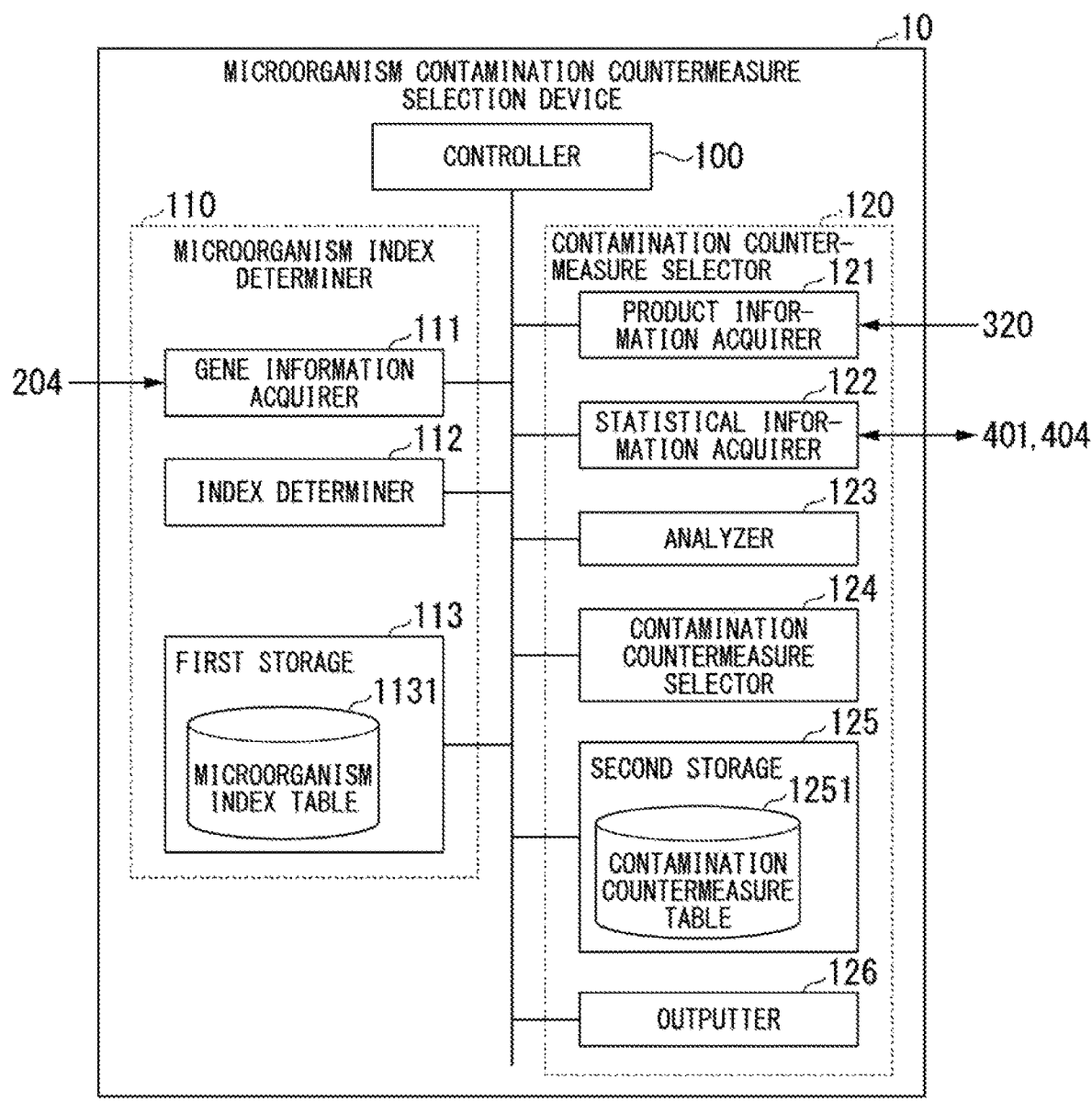
FIG. 2 is a block diagram showing a configuration of a microorganism contamination countermeasure selection device according to one embodiment of the present invention.

FIG. 2 is a block diagram showing a configuration of the microorganism contamination countermeasure selection device 10 according to one embodiment of the present invention. As shown, microorganism contamination countermeasure selection device 10 includes a controller 100, a microorganism index determiner 110, and a contamination countermeasure selector 120.

The controller 100 reads and executes a software program stored in a first storage 113 and a second storage 125, which will be described below, and controls processing by each functional block of the microorganism contamination countermeasure selection device 10. The controller 100 includes a processor, for example, a central processing unit (CPU).

The microorganism index determiner 110 acquires information (gene information) on nucleotide sequences of microorganisms contained in the sample collected from the product from the gene analyzing device 20, and based on the nucleotide sequence and microorganism index table on the basis of the acquired gene information, determines at least one microorganism index corresponding to a nucleotide sequence based on the acquired gene information.

As shown in FIG. 2, the microorganism index determiner 110 includes a gene information acquirer 111, an index determiner 112, and the first storage 113.

The gene information acquirer 111 acquires information (gene information) on nucleotide sequences of microorganisms contained in the sample collected from the product output from a gene information outputter 204 (to be described below) of the gene analyzing device 20 via the communication network 50. The gene information acquirer 111 outputs the acquired gene information to the index determiner 112.

The gene information acquirer 111 includes a communication interface for a communication connection to the gene information outputter 204 of the gene analyzing device 20 via the communication network 50.

The index determiner 112 acquires gene information output from the gene information acquirer 111. The index determiner 112 searches a microorganism index table 1131 stored in the first storage 113 for a nucleotide sequence that matches at least one nucleotide sequence based on the acquired gene information. The index determiner 112 identifies a microorganism index associated with each of the at least one nucleotide sequence that is found. The index determiner 112 determines that the identified at least one microorganism index is a microorganism index corresponding to microorganisms contained in the sample.

The index determiner 112 outputs the determined microorganism index to a statistical information acquirer 122 (to be described below) and an analyzer 123 (to be described below) of the contamination countermeasure selector 120.

The first storage 113 stores in advance the microorganism index table 1131. Here, for example, the microorganism index table 1131 is stored in advance in the first storage 113 by a manual operation by the user.

In addition, the first storage 113 stores various types of data and software programs and the like used in the microorganism contamination countermeasure selection device 10. The first storage 113 is composed of a storage medium, for example, a hard disk drive (HDD), a flash memory, an electrically erasable programmable read only memory (EEPROM), a random access read/write memory (RAM), a read only memory (ROM), or any combination of these storage mediums.

The microorganism index table 1131 is data in which a microorganism index based on features of microorganisms is associated with at least one nucleotide sequence. Here, the table configuration of the microorganism index table 1131 will be described below in detail.

The contamination countermeasure selector 120 selects at least one of contamination countermeasures corresponding to each of the determined microorganism indexes based on the microorganism index determined by the microorganism index determiner 110 and the contamination countermeasure table, and outputs information indicating the selected contamination countermeasure to the user.

As shown in FIG. 2, the contamination countermeasure selector 120 includes a product information acquirer 121, the statistical information acquirer 122, the analyzer 123, a contamination countermeasure selector 124, the second storage 125, and an outputter 126.

The product information acquirer 121 acquires product information on a product from which a sample is collected, which is output from a product information outputter 320 (to be described below) of the product information input device 30 via the communication network 50. The product information acquirer 121 outputs the acquired product information to the statistical information acquirer 122 and the contamination countermeasure selector 124.

The product information acquirer 121 includes a communication interface for a communication connection to the product information outputter 320 of the product information input device 30 via the communication network 50.

The statistical information acquirer 122 acquires a microorganism index output from the index determiner 112.

In addition, the statistical information acquirer 122 acquires production information output from the product information acquirer 121.

The statistical information acquirer 122 outputs at least one of the acquired microorganism index and production information and a request for acquiring statistical information via the communication network 50 to a request receiver 401 (to be described below) of the statistical information database server 40, and requests the statistical information database server 40 to acquire statistical information.

The statistical information acquirer 122 acquires various types of statistical information on contamination countermeasures, which are responses from the statistical information database server 40 with respect to the acquisition request, output from a statistical information outputter 404 (to be described below) of the statistical information database server 40.

The statistical information acquirer 122 outputs the acquired statistical information to the contamination countermeasure selector 124.

The statistical information acquirer 122 includes a communication interface for a communication connection to each of the request receiver 401 and the statistical information outputter 404 of the statistical information database server 40 via the communication network 50.

The analyzer 123 acquires at least one microorganism index output from the index determiner 112.

The analyzer 123 searches the contamination countermeasure table 1251 stored in the second storage 125 for a microorganism index that matches the acquired microorganism index. The analyzer 123 extracts at least one of contamination countermeasures associated with each of the found microorganism indexes.

The analyzer 123 outputs information on a combination of at least one microorganism index used for the search and at least one contamination countermeasure extracted for the microorganism index to the contamination countermeasure selector 124.

The contamination countermeasure selector 124 acquires information on a combination of at least one microorganism index and at least one of contamination countermeasures associated with each of the microorganism indexes, which is output from the analyzer 123.

In addition, the contamination countermeasure selector 124 acquires product information output from the product information acquirer 121 and statistical information output from the statistical information acquirer 122.

The contamination countermeasure selector 124 narrows down contamination countermeasures for information on a combination of the above acquired at least one microorganism index and at least one of contamination countermeasures associated with each of the microorganism indexes using the acquired product information and statistical information. The contamination countermeasure selector 124 selects the narrowed contamination countermeasures as contamination countermeasures against contamination by microorganisms contained in the sample. The contamination countermeasure selector 124 outputs information indicating the selected contamination countermeasure to the outputter 126.

Here, an example of a process of narrowing down contamination countermeasures performed by the contamination countermeasure selector 124 will be described below together with the description of a table configuration of the contamination countermeasure table 1251.

Here, a process of narrowing down contamination countermeasures performed by the contamination countermeasure selector 124 is an optional process. That is, a configuration in which contamination countermeasures extracted by the analyzer 123 are directly selected as contamination countermeasures against contamination by microorganisms contained in the sample may be used. Here, the contamination countermeasure selector 124 may be configured to perform a process of narrowing down contamination countermeasures using only the acquired product information (without using statistical information).

The second storage 125 stores in advance the contamination countermeasure table 1251. Here, for example, the contamination countermeasure table 1251 is stored in advance in the second storage 125 by a manual operation by the user.

In addition, the second storage 125 stores various types of data and software programs and the like used in the microorganism contamination countermeasure selection device 10. The second storage 125 is composed of a storage medium, for example, an HDD, a flash memory, an EEPROM, a RAM, a ROM, or any combination of these storage media.

The contamination countermeasure table 1251 is data in which a contamination countermeasure against contamination by microorganisms is associated with at least one microorganism index. Here, the table configuration of the contamination countermeasure table 1251 will be described below in detail.

The outputter 126 acquires information indicating the selected contamination countermeasure output from the contamination countermeasure selector 124. For example, the outputter 126 outputs information indicating the selected contamination countermeasure to a display (not shown) included in the outputter 126 itself. Thereby, the selected contamination countermeasure against contamination by microorganisms contained in the sample is presented for the user.

The outputter 126 includes a display, for example, a liquid crystal display (LCD), an organic electroluminescence (EL) display, or a cathode ray tube (CRT). In addition, an operation inputter (not shown) and the outputter 126 included in the microorganism contamination countermeasure selection device 10 may be composed of one member having an input and output function, for example, a touch panel.

Here, the outputter 126 may be a communication interface that is connected to communicate with an external device that acquires and output information indicating contamination countermeasures and outputs the information indicating contamination countermeasures to the external device.

[Configuration of Gene Analyzing Device]

Hereinafter, the configuration of the gene analyzing device 20 will be described in more detail with reference to the drawings.

Figure 3:
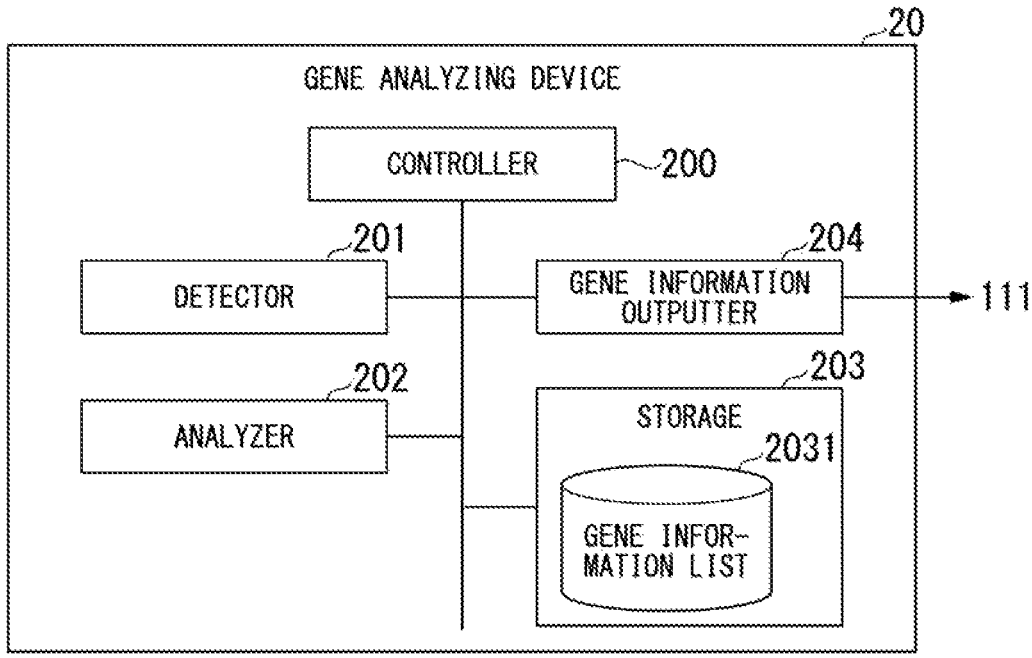
FIG. 3 is a block diagram showing a configuration of a gene analyzing device according to one embodiment of the present invention.

FIG. 3 is a block diagram showing a configuration of the gene analyzing device 20 according to one embodiment of the present invention. As shown, the gene analyzing device 20 includes a controller 200, a detector 201, an analyzer 202, a storage 203, and the gene information outputter 204.

The controller 200 reads and executes a software program stored in the storage 203 to be described below and thus controls processing by each functional block of the gene analyzing device 20. The controller 200 includes a processor, for example, a CPU.

The detector 201 detects microorganisms contained in the sample collected from the product and detects genes (nucleotide sequence) of the detected microorganisms. The detector 201 outputs information indicating the detected nucleotide sequence to the analyzer 202.

As described above, the detector 201 includes a detection device that detects genes (nucleotide sequence) of microorganisms, for example, a cartridge or a reading device including a microarray and an information processing device that analyzes the detected nucleotide sequence, for example, a dedicated computer, and a personal computer.

The analyzer 202 acquires information indicating the nucleotide sequence output from the detector 201. The analyzer 202 performs analysis by searching for a nucleotide sequence that matches at least one nucleotide sequence based on the acquired information in a gene information list 2031 to be described below stored in the storage 203. The analyzer 202 generates information (gene information) indicating at least one nucleotide sequence of the microorganisms, which is an analysis result of microorganisms contained in the sample. The analyzer 202 outputs the generated gene information to the gene information outputter 204.

The storage 203 stores the gene information list 2031 in advance. For example, the gene information list 2031 is stored in advance in the storage 203 by a manual operation by the user.

In addition, the storage 203 stores various types of data and software programs and the like used in the gene analyzing device 20. The storage 203 is composed of a storage medium, for example, an HDD, a flash memory, an EEPROM, a RAM, a ROM, or any combination of these storage media.

The gene information list 2031 is a list of nucleotide sequences that target microorganisms may have. Here, the configuration of the gene information list 2031 will be described below in detail.

The gene information outputter 204 acquires gene information output from the analyzer 202. The gene information outputter 204 outputs the acquired gene information to the gene information acquirer 111 of the microorganism contamination countermeasure selection device 10 via the communication network 50.

The gene information outputter 204 includes a communication interface for a communication connection to the gene information acquirer 111 of the microorganism contamination countermeasure selection device 10 via the communication network 50.

[Configuration of Product Information Input Device]

Hereinafter, the configuration of the product information input device 30 will be described in more detail with reference to the drawings.

Figure 4:
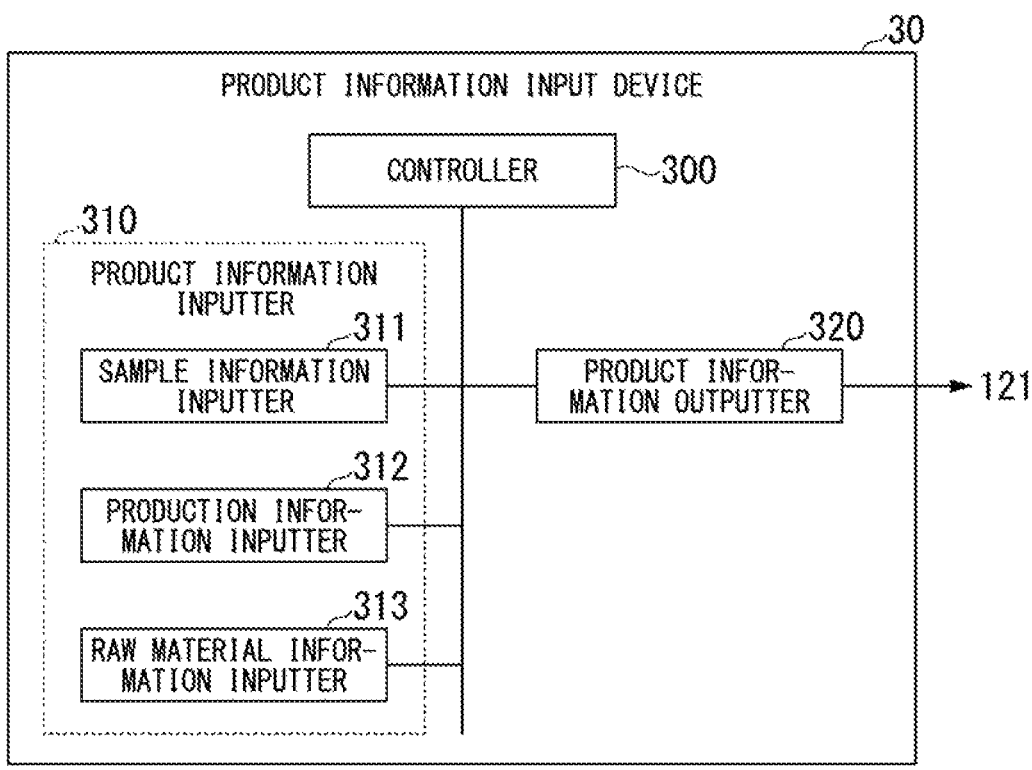
FIG. 4 is a block diagram showing a configuration of a product information input device according to one embodiment of the present invention.

FIG. 4 is a block diagram showing a configuration of the product information input device 30 according to one embodiment of the present invention. As shown, the product information input device 30 includes a controller 300, a product information inputter 310, and the product information outputter 320.

The controller 300 reads and executes a software program stored in a storage (not shown) included in the product information input device 30 and thus controls processing by each functional block of the product information input device 30. The controller 300 includes a processor, for example, a CPU.

The product information inputter 310 is an input interface that receives an input of product information indicating information on a product from which a sample is collected based on an operation input by the user. As described above, the product information includes sample information, production information, and raw material information.

The product information inputter 310 includes a member that can receive an operation input from the user, for example, a keyboard, a mouse, or a pointing device. In addition, a display (not shown) and the product information inputter 310 included in the product information input device 30 may be composed of one member having an input and output function, for example, a touch panel.

Here, the product information inputter 310 may be a communication interface that is connected to communicate with an external device that outputs product information and acquires the product information.

As shown in FIG. 4, the product information inputter 310 includes a sample information inputter 311, a production information inputter 312, and a raw material information inputter 313.

Here, the product information inputter 310 may include only any one or two of the sample information inputter 311, the production information inputter 312, and the raw material information inputter 313.

The sample information inputter 311 acquires sample information indicating information on a sample or sampling of the sample input by an operation input from the user. The sample information inputter 311 outputs the acquired sample information to the product information outputter 320. Here, the configuration of the sample information will be described below in detail.

The production information inputter 312 acquires production information indicating a product from which a sample is collected or information on production of the product, which is input by an operation input from the user. The production information inputter 312 outputs the acquired production information to the product information outputter 320. Here, the configuration of the production information will be described below in detail.

The raw material information inputter 313 acquires raw material information indicating information on raw materials used a product from which a sample is collected, which is input by an operation input from the user. The raw material information inputter 313 outputs the acquired raw material information to the product information outputter 320. Here, the configuration of raw material information will be described below in detail.

The product information outputter 320 acquires sample information output from the sample information inputter 311, production information output from the production information inputter 312, and raw material information output from the raw material information inputter 313. The product information outputter 320 outputs the acquired sample information, production information, and raw material information to the product information acquirer 121 of the microorganism contamination countermeasure selection device 10 via the communication network 50.

The product information outputter 320 includes a communication interface for a communication connection to the product information acquirer 121 of the microorganism contamination countermeasure selection device 10 via the communication network 50.

[Configuration of Statistical Information Database Server]

Hereinafter, the configuration of the statistical information database server 40 will be described in more detail with reference to the drawings.

Figure 5:
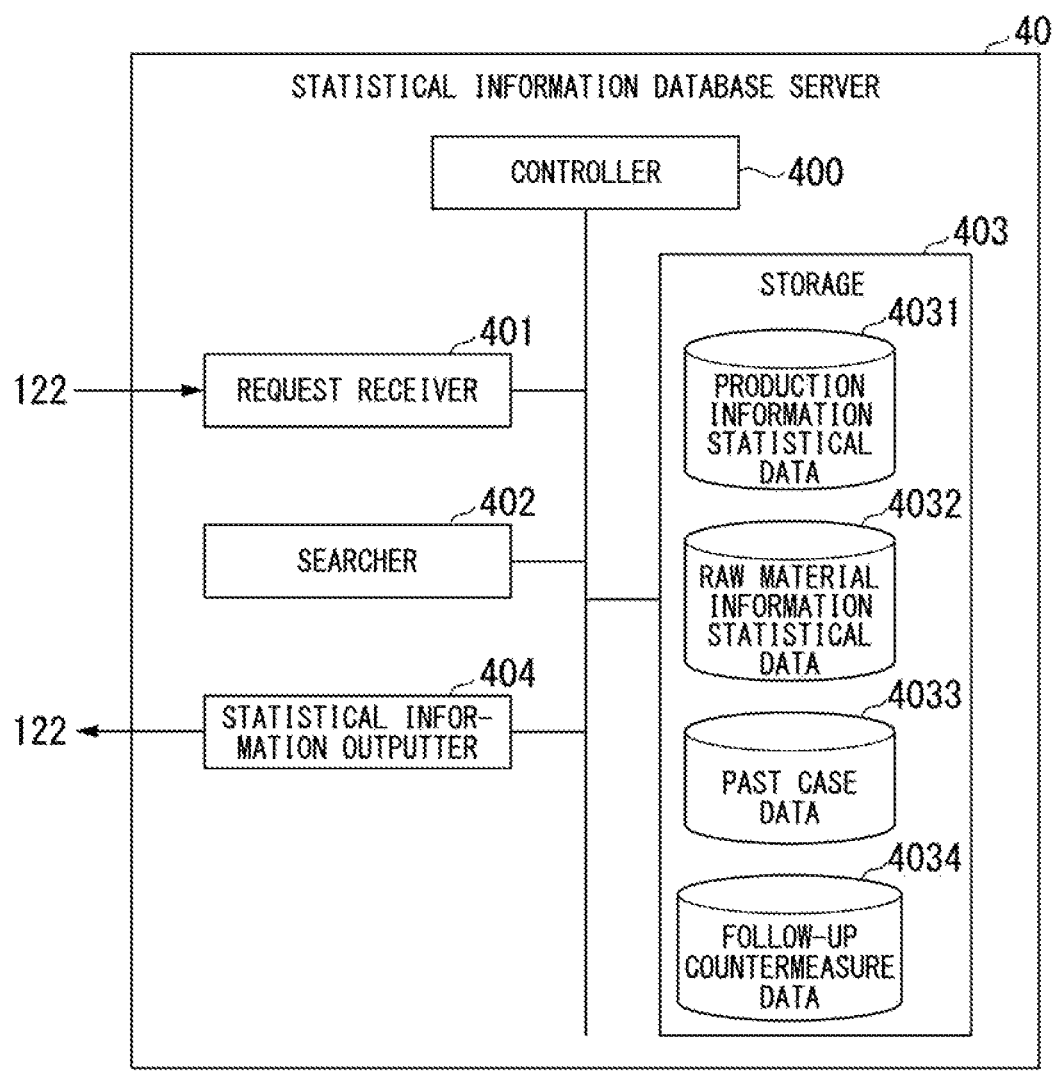
FIG. 5 is a block diagram showing a configuration of a statistical information database server according to one embodiment of the present invention.

FIG. 5 is a block diagram showing a configuration of the statistical information database server 40 according to one embodiment of the present invention. As shown, the statistical information database server 40 includes a controller 400, a request receiver 401, a searcher 402, a storage 403, and the statistical information outputter 404.

The controller 400 reads and executes a software program stored in the storage 403 (to be described below) and thus controls processing by each functional block of the statistical information database server 40. The controller 400 includes a processor, for example, a CPU.

The request receiver 401 acquires at least one of the microorganism indexes and product information and a request for acquiring statistical information, which are output from the statistical information acquirer 122 of the microorganism contamination countermeasure selection device 10. The request receiver 401 outputs the acquired microorganism index and product information to the searcher 402.

The request receiver 401 includes a communication interface for a communication connection to the statistical information acquirer 122 of the microorganism contamination countermeasure selection device 10 via the communication network 50.

The searcher 402 acquires at least one of the microorganism indexes and product information output from the request receiver 401. The searcher 402 searches a database of various types of statistical information stored in the storage 403 for various types of statistical information associated with each of at least one of the acquired microorganism index and product information.

Here, various types of statistical information stored in the storage 403 are production information statistical data 4031, raw material information statistical data 4032, past case data 4033, and follow-up countermeasure data 4034, which will be described below.

Here, the searcher 402 stores the product information used in the above search in a database of various types of statistical information stored in the storage 403. Thereby, past product information is stored in the storage 403.

When various types of statistical information associated with at least one of the acquired microorganism index and product information are found, the searcher 402 outputs the found various types of statistical information to the statistical information outputter 404.

The storage 403 stores various types of statistical information, that is, the production information statistical data 4031, the raw material information statistical data 4032, the past case data 4033, and the follow-up countermeasure data 4034 shown in FIG. 5.

Here, the storage 403 may store any one, two, or three types of statistical information among four types of statistical information including the production information statistical data 4031, the raw material information statistical data 4032, the past case data 4033, and the follow-up countermeasure data 4034.

Here, these various types of statistical information may be information in which information based on information used in a contamination countermeasure selection process that is performed in the past by the microorganism contamination countermeasure selection device 10 is automatically stored or may be information that is stored by a manual operation by the user.

The storage 403 stores various types of data and software programs and the like used in the statistical information database server 40. The storage 403 is composed of a storage medium, for example, an HDD, a flash memory, an EEPROM, a RAM, a ROM, or any combination of these storage media.

The production information statistical data 4031 is data in which production information used in past contamination countermeasure selection is stored. Here, the configuration of the production information statistical data 4031 will be described below in detail.

The raw material information statistical data 4032 is data in which raw material information used in past contamination countermeasure selection is stored. Here, the configuration of the raw material information statistical data 4032 will be described below in detail.

The past case data 4033 is data in which information on past cases of contamination countermeasure selection is stored.

The follow-up countermeasure data 4034 is data in which the contamination countermeasure selected in each past case included in the past case data 4033 is stored. Here, the configuration of the follow-up countermeasure data 4034 will be described below in detail.

The statistical information outputter 404 acquires various types of statistical information output from the searcher 402. The statistical information outputter 404 outputs the acquired various types of statistical information to the statistical information acquirer 122 of the microorganism contamination countermeasure selection device 10 via the communication network 50.

The statistical information outputter 404 includes a communication interface for a communication connection to the statistical information acquirer 122 of the microorganism contamination countermeasure selection device 10 via the communication network 50.

[Operations of Microorganism Contamination Countermeasure Selection Device]

Hereinafter, an example of operations of the microorganism contamination countermeasure selection device 10 will be described with reference to the drawings.

Figure 6:
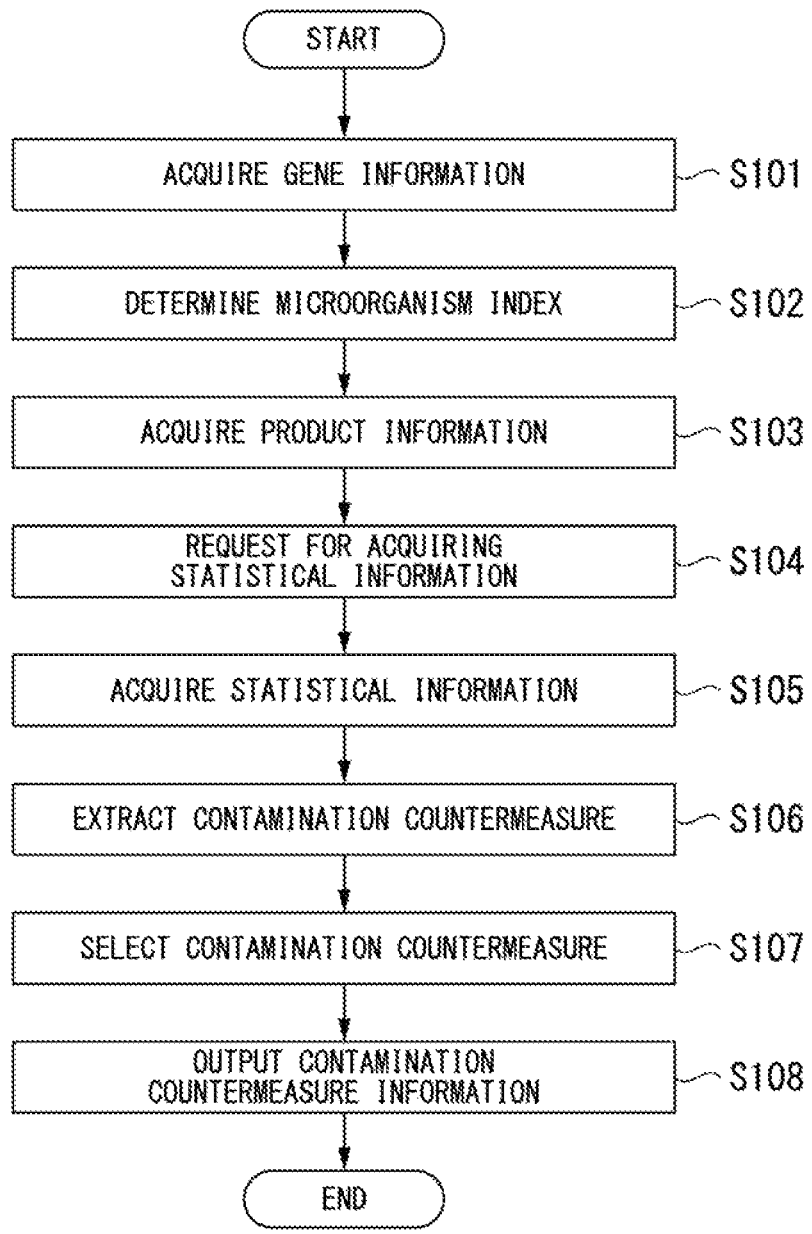
FIG. 6 is a flowchart showing operations of the microorganism contamination countermeasure selection device according to one embodiment of the present invention.

FIG. 6 is a flowchart showing operations of the microorganism contamination countermeasure selection device 10 according to one embodiment of the present invention. This flowchart starts when information (gene information) indicating nucleotide sequences of microorganisms contained in a sample collected from a product is output from the gene information outputter 204 of the gene analyzing device 20 to the gene information acquirer 111 of the microorganism contamination countermeasure selection device 10.

(Step S101)

The gene information acquirer 111 of the microorganism contamination countermeasure selection device 10 acquires gene information output from the gene information outputter 204 of the gene analyzing device 20 via the communication network 50. The gene information acquirer 111 outputs the acquired gene information to the index determiner 112. Then, the process advances to Step S102.

(Step S102)

The index determiner 112 of the microorganism contamination countermeasure selection device 10 acquires gene information output from the gene information acquirer 111. The index determiner 112 searches the microorganism index table 1131 stored in the first storage 113 for a nucleotide sequence that matches the nucleotide sequence based on the acquired gene information. The index determiner 112 identifies at least one microorganism index associated with the found nucleotide sequence. The index determiner 112 determines that the identified microorganism index is a microorganism index corresponding to microorganisms contained in the sample.

The index determiner 112 outputs the determined microorganism index to the statistical information acquirer 122 and the analyzer 123 (to be described below) of the contamination countermeasure selector 120. Then, the process advances to Step S103.

(Step S103)

The product information acquirer 121 of the microorganism contamination countermeasure selection device 10 acquires product information on a product from which a sample is collected, which is output from the product information outputter 320 of the product information input device 30, via the communication network 50. The product information acquirer 121 outputs the acquired product information to the contamination countermeasure selector 124. Then, the process advances to Step S104.

(Step S104)

The statistical information acquirer 122 of the microorganism contamination countermeasure selection device 10 acquires a microorganism index output from the index determiner 112. In addition, the statistical information acquirer 122 acquires production information output from the product information acquirer 121. The statistical information acquirer 122 outputs at least one of the acquired microorganism index and product information and a request for acquiring statistical information to the request receiver 401 (to be described below) of the statistical information database server 40 via the communication network 50, and thereby requests the statistical information database server 40 to acquire statistical information. Then, the process advances to Step S105.

(Step S105)

The statistical information acquirer 122 of the microorganism contamination countermeasure selection device 10 acquires various types of statistical information on contamination countermeasures, which are responses from the statistical information database server 40 with respect to the acquisition request, output from the statistical information outputter 404 of the statistical information database server 40. The statistical information acquirer 122 outputs the acquired statistical information to the contamination countermeasure selector 124. Then, the process advances to Step S106.

(Step S106)

The analyzer 123 of the microorganism contamination countermeasure selection device 10 acquires at least one microorganism index output from the index determiner 112. The analyzer 123 searches the contamination countermeasure table 1251 stored in the second storage 125 for a microorganism index that matches the acquired microorganism index. The analyzer 123 extracts at least one of contamination countermeasures associated with each of the found microorganism indexes. The analyzer 123 outputs information on a combination of at least one microorganism index used for the search and at least one contamination countermeasure extracted for the microorganism index to the contamination countermeasure selector 124. Then, the process advances to Step S107.

(Step S107)

The contamination countermeasure selector 124 of the microorganism contamination countermeasure selection device 10 acquires information on a combination of at least one microorganism index and at least one of contamination countermeasures associated with each of the microorganism indexes, which is output from the analyzer 123. In addition, the contamination countermeasure selector 124 acquires product information output from the product information acquirer 121 and statistical information output from the statistical information acquirer 122.

The contamination countermeasure selector 124 narrows down contamination countermeasures for information on a combination of the acquired at least one microorganism index and at least one of contamination countermeasures associated with each of the microorganism indexes using the acquired product information and statistical information. The contamination countermeasure selector 124 selects the narrowed contamination countermeasures as contamination countermeasures against contamination by microorganisms contained in the sample. The contamination countermeasure selector 124 outputs information indicating the selected contamination countermeasure to the outputter 126. Then, the process advances to Step S108.

(Step S108)

The outputter 126 of the microorganism contamination countermeasure selection device 10 acquires information indicating the selected contamination countermeasure output from the contamination countermeasure selector 124. For example, the outputter 126 outputs information indicating the selected contamination countermeasure to a display included in the outputter 126 itself.

Thus, the process of this flowchart ends.

[Configuration of Microorganism Index]

Hereinafter, the configuration of a microorganism index will be described with reference to the drawings.

Figure 7:
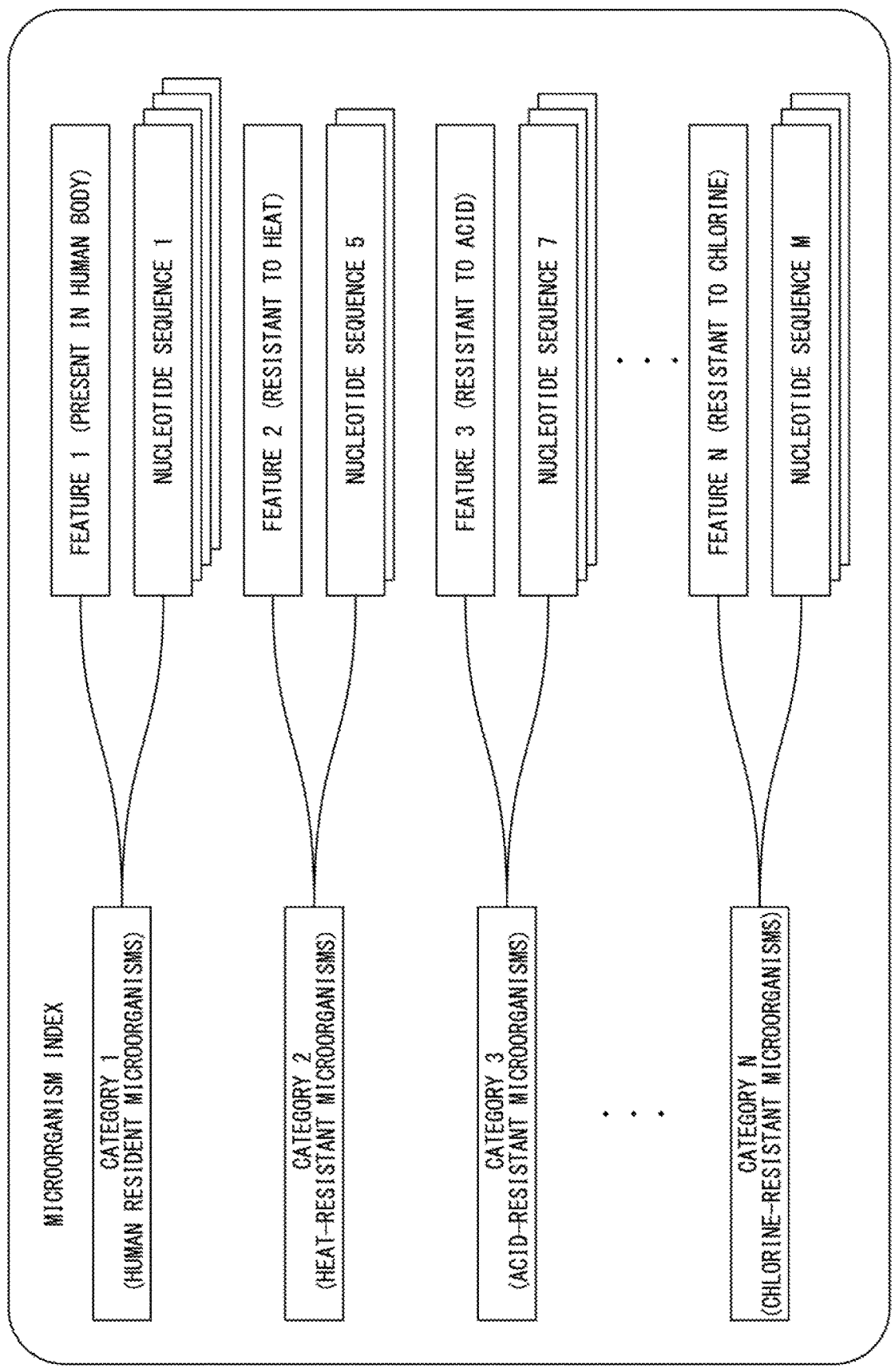
FIG. 7 is a schematic diagram showing an overview of a configuration of a microorganism index stored in the microorganism contamination countermeasure selection device according to one embodiment of the present invention.

FIG. 7 is a schematic diagram showing an overview of a configuration of a microorganism index stored in the microorganism contamination countermeasure selection device 10 according to one embodiment of the present invention.

The microorganism index is a database that is used to identify features found in contaminating microorganisms. For example, in the example shown in FIG. 7, regarding the value of the microorganism index, there are N values from "category 1" to "category N." A microorganism index to which each of microorganisms contained in the sample corresponds is determined, and a contamination countermeasure is selected based on the determined microorganism index.

Here, it is determined that a plurality of microorganism indexes correspond to one microorganism in some cases.

As shown in FIG. 7, one piece of feature information indicating a feature found based on contamination by microorganisms is associated with one microorganism index in a one-to-one relationship. In addition, at least one type of nucleotide sequence information indicating a specific nucleotide sequence corresponding to the above feature is associated with one microorganism index in a one-to-many relationship. Therefore, a specific nucleotide sequence associated with one feature of microorganisms may be a combination of a plurality of types of nucleotide sequences.

As shown in FIG. 7, for example, one "feature 1" which is a feature of "(microorganisms) present in a human body" is associated with a microorganism index of "category 1." Therefore, microorganisms determined as having the microorganism index of "category 1" are "human resident microorganisms."

In addition, for example, four types of nucleotide sequences including "nucleotide sequence 1," "nucleotide sequence 2," "nucleotide sequence 3," and "nucleotide sequence 4" are associated with the microorganism index of "category 1."

In addition, as shown in FIG. 7, for example, one "feature N" which is a feature of "(microorganisms) resistant to chlorine" is associated with the microorganism index of "category N." Therefore, microorganisms determined as having the microorganism index of "category N" are "chlorine-resistant microorganisms."

In addition, for example, three types of nucleotide sequences including "nucleotide sequence M," "nucleotide sequence M+1," and "nucleotide sequence M+2" are associated with the microorganism index of "category N".

With the above configuration, when a certain specific nucleotide sequence (or a combination of certain specific nucleotide sequences) is detected from microorganisms contained in the sample, the microorganism index can be identified from the detected nucleotide sequence. Therefore, it is possible to identify features (found based on microorganism contamination) associated with the identified microorganism index.

Here, "features" referred to here mean features found based on microorganism contamination, which is determined for certain purposes. Examples of features include characteristics exhibited by microorganisms, and contamination routes of the microorganisms. More specifically, for example, when an inspection is performed for the purpose for determining whether a heat treatment is appropriately performed in a certain food production line, features thereof include "heat resistance."

Based on the above concept of the microorganism index, in selecting appropriate contamination countermeasures, it is only necessary that features found by microorganism contamination be the same, but the microorganisms need not necessarily be the same species or genus. Therefore, even if bacteria, viruses, and fungi from which the same features can be found are mixed, when there is a (specific) nucleotide sequence that is commonly found among them, the nucleotide sequence can be a specific nucleotide sequence (associated with a microorganism index).

Here, "specific nucleotide sequence" referred to here refers to a part or all of nucleotide sequences commonly found in microorganisms that can provide features (found based on microorganism contamination) associated with microorganism indexes.

[Creation of Microorganism Index]

Hereinafter, creation of a microorganism index will be described. As will be described below, in order to create the microorganism index, first, "(i) set of features" will be performed and then "(ii) set of specific nucleotide sequences" will be performed. Here, the creation of the microorganism index is performed in advance by the user.

(i) Set of Features

Information set in the microorganism index greatly varies depending on the reason for which a microorganism index is used, that is, a purpose for identifying features of microorganisms contained in the sample. Therefore, if subjects for which measures such as a contamination countermeasure are to be taken are different, features that are focused on are also different. Therefore, on the assumption that features are set for microorganism indexes, first, it is necessary to establish a purpose for identifying features of microorganisms contained in the sample. That is, features are appropriately set according to any purpose for identifying features of microorganisms contained in the sample.

Here, the degree to which features are subdivided that is set for a microorganism index is arbitrarily set according to a purpose for identifying features of microorganisms contained in the sample. For example, it is assumed that there are a case in which it is desired to identify only whether toxin is produced and a case in which it is desired to identify additionally whether a heat-resistant toxin is produced or a heat-labile toxin is produced in a distinctive manner. In this case, for example, in the former case, a specific nucleotide sequence is set for a microorganism index based on a nucleotide sequence common to "*Staphylococcus, Salmonella, Clostridium perfringens,* and *Bacillus cereus.*" On the other hand, in the latter case, subdivision into "*Staphylococcus, Bacillus cereus*" and "*Salmonella, Clostridium perfringens*" is additionally performed, and a specific nucleotide sequence is set for a microorganism index based on a nucleotide sequence common to each of the subdivisions.

Here, there is no need to include only bacteria as in the above examples, and the above classification may include fungi and viruses.

In addition, depending on a purpose for identifying features of microorganisms contained in the sample, features may be classified according to a difference in contamination routes. For example, when a heat-resistant toxin is detected and it is desired to identify whether the heat-resistant toxin is derived from a human, for example, "feature A" of "human-derived heat-resistant toxin" and "specific nucleotide sequence A" specifically found in *Staphylococcus aureus* or the like may be assigned to one microorganism index (category A), and "feature B" of "non-human-derived heat-resistant toxin" and "specific nucleotide sequence B" specifically found in *Bacillus cereus* or the like may be assigned to one microorganism index (category B).

Here, the specific nucleotide sequence A or the specific nucleotide sequence B may be a combination of a plurality of specific nucleotide sequences.

(ii) Set of Specific Nucleotide Sequence

The specific nucleotide sequence is set for a microorganism index based on the nucleotide sequence commonly found in microorganisms constituting each of the microorganism groups that provide features set in the above (i). For example, the nucleotide sequence commonly found in microorganisms constituting the microorganism group can be set from the same area in nucleic acids of these microorganisms. In addition, when the specific nucleotide sequence is composed of a combination of a plurality of specific nucleotide sequences, it may be set from one range of the same area or may be set from a plurality of ranges.

Here, the nucleotide length of the specific nucleotide sequence can be arbitrarily set as long as it is equal to or shorter than the nucleotide length of the nucleotide sequence commonly found in microorganisms constituting the microorganism group, and when used as a probe, a length of 5 to 100 bases is preferable, and a length of 20 to 30 bases is more preferable.

Here, the specific nucleotide sequence is assumed to be shorter than the nucleotide length of the nucleotide sequence commonly found in microorganisms constituting the microorganism group.

[Configuration of Gene Information List]

Hereinafter, the configuration of the gene information list 2031 will be described with reference to the drawings.

FIG. 8 is a diagram showing a configuration of the gene information list 2031 stored in the gene analyzing device 20 according to one embodiment of the present invention. As shown, the gene information list 2031 is data including the column of an item of "nucleotide sequence."

The gene information list 2031 exemplified in FIG. 8 corresponds to the specific nucleotide sequence associated with the microorganism index shown in FIG. 7 and is a list of information indicating M+2 specific nucleotide sequences from nucleotide sequence 1 to nucleotide sequence M+2.

The analyzer 202 of the gene analyzing device 20 acquires information indicating the nucleotide sequence output from the detector 201, and searches the gene information list 2031 shown in FIG. 8 for a nucleotide sequence that matches at least one nucleotide sequence based on the acquired information.

Here, when a nucleotide sequence that matches the nucleotide sequence based on the acquired information is not included in the gene information list 2031, the analyzer 202 determines that the target microorganisms are not included in the sample and discards information indicating the nucleotide sequence.

FIG. 9 is a diagram showing a configuration of the microorganism index table 1131 stored in the microorganism contamination countermeasure selection device 10 according to one embodiment of the present invention. As shown, the microorganism index table 1131 is 2D tabular data including columns of two items of "microorganism index" and "nucleotide sequence."

The microorganism index table 1131 exemplified in FIG. 9 is a table which corresponds to the specific nucleotide sequence associated with the microorganism index shown in FIG. 7 and in which information indicating N microorganism indexes from category 1 to category N is associated with information indicating M+2 specific nucleotide sequences from nucleotide sequence 1 to nucleotide sequence M+2 in a one-to-many relationship.

As shown in FIG. 9, for example, a microorganism index of "category 1" is associated with nucleotide sequences of "nucleotide sequence 1," "nucleotide sequence 2," "nucleotide sequence 3," and "nucleotide sequence 4." In addition, as shown in FIG. 9, for example, a microorganism index of "category N" is associated with nucleotide sequences of "nucleotide sequence M," "nucleotide sequence M+1," and "nucleotide sequence M+2."

The index determiner 112 of the microorganism contamination countermeasure selection device 10 acquires gene information output from the gene information acquirer 111 and searches the microorganism index table 1131 shown in FIG. 9 for a nucleotide sequence that matches at least one nucleotide sequence based on the acquired gene information. The index determiner 112 identifies a microorganism index associated with each of the at least one nucleotide sequence that is found and determines that the identified at least one microorganism index is a microorganism index corresponding to microorganisms contained in the sample.

[Configuration of Contamination Countermeasure Table]

Hereinafter, the configuration of the contamination countermeasure table 1251 will be described with reference to the drawings.

FIG. 10 is a diagram showing a configuration of the contamination countermeasure table 1251 stored in the microorganism contamination countermeasure selection device 10 according to one embodiment of the present invention. As shown, the contamination countermeasure table 1251 is 2D tabular data in which rows of N items indicating the microorganism indexes from "category 1 (human resident)" to "category N (chlorine resistance)" are associated with L columns indicating the contamination countermeasures from "countermeasure 1 (discarding lots)" to "countermeasure L (change raw materials)."

The contamination countermeasure table 1251 exemplified in FIG. 10 is a table which corresponds to the microorganism index shown in FIG. 7 and in which it is defined whether L contamination countermeasures from countermeasure 1 to countermeasure L are necessary for information indicating N microorganism indexes from category 1 to category N.

Here, in the contamination countermeasure table 1251 exemplified in FIG. 10, "O" indicates "necessary contamination countermeasure," "Δ" indicates "necessary contamination countermeasure depending on conditions," and "×" indicates "unnecessary contamination countermeasure."

As shown in FIG. 10, for example, for "category 1 (human resident (microorganisms))," "Δ" is defined for "countermeasure 1 (discarding lots)," "O" is defined for "countermeasure 2 (sampling discarding)," "Δ" is defined for "countermeasure 3 (CIP cleaning)," "Δ" is defined for "countermeasure 4 (SIP sterilization)," "Δ" is defined for "countermeasure 5 (disassembling and cleaning production lines)," and "×" is defined for "countermeasure L (change raw materials)." In addition, as shown in FIG. 10, for example, for "category N (chlorine-resistant (microorganisms))," "O" is defined for "countermeasure 1 (discarding lots)," "O" is defined for "countermeasure 2 (sampling discarding)," "O" is defined for "countermeasure 3 (CIP cleaning)," "Δ" is defined for "countermeasure 4 (SIP sterilization)," "O" is defined for "countermeasure 5 (disassembling and cleaning production lines)" and "O" is defined for "countermeasure L (change raw materials)."

The analyzer 123 of the microorganism contamination countermeasure selection device 10 acquires at least one microorganism index output from the index determiner 112 and searches the contamination countermeasure table 1251 shown in FIG. 10 for a microorganism index that matches the acquired microorganism index.

The analyzer 123 extracts "necessary contamination countermeasure" (contamination countermeasure defined as "O") and "necessary contamination countermeasure depending on conditions" (contamination countermeasure defined as "Δ") which are associated with each of the found microorganism indexes. The analyzer 123 outputs information on a combination of at least one microorganism index used for the search and the "necessary contamination countermeasure" and "necessary contamination countermeasure depending on conditions" extracted from the microorganism index to the contamination countermeasure selector 124.

The contamination countermeasure selector 124 acquires information on a combination of the microorganism index and contamination countermeasure output from the analyzer 123. In addition, the contamination countermeasure selector 124 acquires product information output from the product information acquirer 121 and statistical information output from the statistical information acquirer 122.

The contamination countermeasure selector 124 performs a process of narrowing down contamination countermeasures for "necessary contamination countermeasure depending on conditions" (contamination countermeasure defined as "Δ") within information indicating the contamination countermeasure acquired from the analyzer 123 using the acquired product information and statistical information. Here, an example of a process of narrowing down contamination countermeasures will be described below.

The contamination countermeasure selector 124 selects "necessary contamination countermeasure" (contamination countermeasure defined as "O") and "necessary contamination countermeasure depending on conditions" (contamination countermeasure defined as "Δ") narrowed down in the process of narrowing down contamination countermeasures within information on a combination of the microorganism index and contamination countermeasure acquired from the analyzer 123 as contamination countermeasures against contamination by microorganisms contained in the sample.

That is, the "necessary contamination countermeasure" (contamination countermeasure defined as "O") is selected as a contamination countermeasure that needs to be performed regardless of the product information and statistical information, but the "necessary contamination countermeasure depending on conditions" (contamination countermeasure defined as "Δ") is selected as a necessary contamination countermeasure depending on conditions based on the product information and statistical information.

[Process of Narrowing Down Contamination Countermeasures]

Hereinafter, an example of a process of narrowing down contamination countermeasures performed by the contamination countermeasure selector 124 of the microorganism contamination countermeasure selection device 10 will be described.

For example, the contamination countermeasure selector 124 acquires production information indicating the fact that a product from which a sample is collected using a raw material with a lot number of "A" is produced from the product information input device 30.

In addition, for example, the contamination countermeasure selector 124 acquires statistical information showing information indicating the fact that the same product as a product from which a sample is collected using a raw material with a lot number of "A" in the past is produced and details of the (past) contamination countermeasure performed at that time and results thereof.

In the above case, for example, when no microorganisms having the same features are detected in the past microorganism detection results, the contamination countermeasure selector 124 determines that contamination occurred and selects a necessary contamination countermeasure.

On the other hand, in the above case, for example, when microorganisms having the same features are detected in the past microorganism detection results and there are cases in which no problem has occurred even though no specific contamination countermeasure is performed, the contamination countermeasure selector 124 determines that no contamination countermeasure is necessary.

In this manner, the contamination countermeasure selector 124 can perform a process of narrowing down contamination countermeasures using product information such as sample information on a product from which a sample is collected, production information, and raw material information, and statistical information such as statistical data of past production information, statistical data of past raw material information, past case data, and follow-up countermeasure data in past cases.

In addition, for example, the contamination countermeasure selector 124 selects a contamination countermeasure based on the following conditions set in advance based on the statistical information.

When it is determined that a human resident and gram negative index is assigned, no problems with other production lots occur in raw material lots used, and product information shows a high acidity of the product and a microorganism growth risk is low after shipping, a follow-up countermeasure of discarding lots is selected.

A case in which a spore formation index is repeatedly assigned in the same production line is repeated within half a year. In addition, in the case that is not limited to a case in which the same operator is in charge of production according to production information statistical data, a countermeasure of disassembling and cleaning the production line is selected because the production environment is suspected of being contaminated.

When microorganisms to which a biofilm formation index is assigned are detected, countermeasures of CIP cleaning and SIP sterilization are selected for the first time. When this case is repeated within a certain period, it is determined that formation of a biofilm has not been reduced, and a countermeasure of changing the sterilization method is selected.

When microorganisms to which an alcohol resistance index is assigned are detected in a factory in which alcohol cleaning is regularly performed to clean the production environment, in order to remove resistant bacteria, a countermeasure of changing the sterilization method (for example, switching from alcohol cleaning to chlorine cleaning) is selected.

When microorganisms determined as having a protozoa index are detected, it is desirable to select a countermeasure of discarding the total amount in addition to discarding lots. Since production raw water is the most suspicious as a protozoa contamination route, a countermeasure of CIP cleaning in a production water treatment facility is taken and a countermeasure of increasing the frequency of filter deterioration check is selected.

If a certain specific lot raw material is used, when contamination by microorganisms to which a hygrophilc index is assigned is found, lots are discarded and a countermeasure of considering change of a raw material source is selected. On the other hand, when the same raw material is used in other factories but the same case does not occur, it is desirable to select a countermeasure of checking humidity management in a production area in which contamination occurs.

[Configuration of Sample Information]

Hereinafter, the configuration of sample information will be described with reference to the drawings.

FIG. 11 is a diagram showing a configuration of sample information input to the product information input device 30 according to one embodiment of the present invention. As shown, the sample information includes information on a sample or sampling of the sample such as "sampling date/time," "sampling amount," "sampling method," "operator," "inspection lot," "inspection method," and "inspection reagent lot."

The sample information inputter 311 of the product information input device 30 acquires the sample information, which is, for example, information on a sample or sampling of the sample shown in FIG. 11, input by an operation input from the user.

[Configuration of Production Information]

Hereinafter, the configuration of production information will be described with reference to the drawings.

FIG. 12 is a diagram showing a configuration of production information input to the product information input device 30 according to one embodiment of the present invention. As shown, the production information includes information on a product from which a sample is collected or production of the product such as "processing temperature," "intermediate inspection result," "production line," "processing date," "preparation date," "processing start time," "processing end time," "operator," "production environment inspection result," "sterilization temperature," "sterilization method," "production lot," "production water inspection result," "appearance inspection result," and "sensory inspection result."

The production information inputter 312 of the product information input device 30 acquires production information, which is, for example, information on a product from which a sample is collected or production of the product shown in FIG. 12, input by an operation input from the user.

[Configuration of Raw Material Information]

Hereinafter, the configuration of raw material information will be described with reference to the drawings.

FIG. 13 is a diagram showing a configuration of raw material information input to the product information input device 30 according to one embodiment of the present invention. As shown, the raw material information includes information on raw materials used for a product from which a sample is collected such as "production area," "processing area," "processing date," "expiration date," "lot number," "storage conditions," "storage status," "inspection history," "product type," "delivery specifications," "delivery date," and "acceptance inspection result."

The raw material information inputter 313 of the product information input device 30 acquires raw material information, which is, for example, information on raw materials used for a product from which a sample is collected shown in FIG. 13, input by an operation input from the user.

[Configuration of Production Information Statistical Data]

Hereinafter, the configuration of the production information statistical data 4031 will be described with reference to the drawings.

FIG. 14 is a diagram showing a configuration of the production information statistical data 4031 stored in the statistical information database server 40 according to one embodiment of the present invention. As shown, the production information statistical data 4031 is data in which production information used in past contamination countermeasure selection is stored such as "processing temperature," "intermediate inspection result," "production line," "processing date," "preparation date," "processing start time," "processing end time," "operator," "production environment inspection result," "sterilization temperature," "sterilization method," "production lot," "production water inspection result," "appearance inspection result," and "sensory inspection result."

Here, in the configuration, a microorganism index may be associated with each piece of data included in the production information statistical data 4031. Thereby, the microorganism contamination countermeasure selection device 10 can acquire production information in the past microorganism contamination countermeasure selection process in which the same microorganism index as the microorganism index determined in the microorganism contamination countermeasure selection process is determined and perform a process of narrowing down contamination countermeasures based on the acquired production information.

[Configuration of Raw Material Information Statistical Data]

Hereinafter, the configuration of the raw material information statistical data 4032 will be described with reference to the drawings.

FIG. 15 is a diagram showing a configuration of the raw material information statistical data 4032 stored in the statistical information database server 40 according to one embodiment of the present invention. As shown, the raw material information statistical data 4032 is data in which raw material information used in the past contamination countermeasure selection is stored such as "production area," "processing area," "processing date," "expiration date," "lot number," "storage conditions," "storage status," "inspection history," "product type," "delivery specifications," "delivery date," and "acceptance inspection result."

Here, in the configuration, a microorganism index may be associated with each piece of data included in the raw material information statistical data 4032. Thereby, the microorganism contamination countermeasure selection device 10 can acquire raw material information in the past microorganism contamination countermeasure selection process in which the same microorganism index as the microorganism index determined in the microorganism contamination countermeasure selection process is determined and perform a process of narrowing down contamination countermeasures based on the acquired raw material information.

[Configuration of Follow-Up Countermeasure Data]

Hereinafter, the configuration of the follow-up countermeasure data 4034 will be described with reference to the drawings.

FIG. 16 is a diagram showing a configuration of the follow-up countermeasure data 4034 stored in the statistical information database server 40 according to one embodiment of the present invention. As shown, the follow-up countermeasure data 4034 is data in which the selected contamination countermeasure in the past case of contamination countermeasure selection is stored such as "discarding lots," "sampling discarding," "CIP cleaning," "SIP sterilization," "disassembling and cleaning production lines," "operator hygiene management," "discarding (remaining) raw materials," "alerting other factories," "change sterilization conditions," "change sterilization method," "change cleaning agent," and "change raw materials."

Here, in the configuration, a microorganism index may be associated with each piece of data included in the follow-up countermeasure data 4034. Thereby, the microorganism contamination countermeasure selection device 10 can acquire a contamination countermeasure in the past microorganism contamination countermeasure selection process in which the same microorganism index as the microorganism index determined in the microorganism contamination countermeasure selection process is determined and select a contamination countermeasure based on the acquired contamination countermeasure.

As described above, the microorganism contamination countermeasure selection device 10 according to the present embodiment includes a gene information acquirer configured to acquire gene information (information indicating nucleotide sequences) indicating information on genes of microorganisms contained in the sample. In addition, the microorganism contamination countermeasure selection device 10 according to the present embodiment includes an index determiner configured to determine at least one microorganism index corresponding to the gene information acquired by the gene information acquirer based on the gene information acquired by the gene information acquirer and a microorganism index table in which a microorganism index based on features of microorganisms is associated with at least one piece of gene information. In addition, the microorganism contamination countermeasure selection device 10 according to the present embodiment includes a contamination countermeasure selector configured to select at least one of contamination countermeasures corresponding to each of the microorganism indexes determined by the index determiner based on the microorganism index determined by the index determiner and a contamination countermeasure table in which a contamination countermeasure against contamination by microorganisms is associated with at least one microorganism index.

In addition, as described above, the microorganism contamination countermeasure selection device 10 according to the present embodiment further includes a product information acquirer configured to acquire product information on a product from which a sample is collected, and the contamination countermeasure selector selects a contamination countermeasure based on the product information.

In addition, as described above, the microorganism contamination countermeasure selection device 10 according to the present embodiment further includes a statistical information acquirer configured to acquire statistical information including at least one of product information used in past contamination countermeasure selection and past contamination countermeasure implementation cases, and the contamination countermeasure selector selects a contamination countermeasure based on the statistical information.

With the above configuration, the microorganism contamination countermeasure selection device 10 according to the present embodiment can select an appropriate follow-up countermeasure (contamination countermeasure) without identifying the species of contaminating microorganisms.

Since it is not necessary to identify the species of contaminating microorganisms, the microorganism contamination countermeasure selection device 10 according to the present embodiment can reduce the inspection time and inspection cost, and select an appropriate follow-up countermeasure without the need for an inspector with expertise. Thereby, the microorganism contamination countermeasure selection device 10 according to the present embodiment can reduce economic loss when a contamination accident occurs.

In addition, since it is not necessary to identify the species of contaminating microorganisms, even if unknown microorganisms are contaminated in the product, the microorganism contamination countermeasure selection device 10 according to the present embodiment selects a contamination countermeasure associated with the nucleotide sequence of the unknown microorganisms, and thus can present an appropriate contamination countermeasure for the user.

In addition, since it is not necessary to identify the species of contaminating microorganisms, in the microorganism contamination countermeasure selection device 10 according to the present embodiment, expertise regarding identification of microorganisms is not necessary, it is not necessary to make a specialized inspector resident, for example, in the organization to which the user belongs, and additionally, it is not necessary to train such a specialized inspector.

In addition, since it is not necessary to identify the species of contaminating microorganisms, in the microorganism contamination countermeasure selection device 10 according to the present embodiment, a rapid contamination countermeasure is possible, for example, even for products with a short expiration date, it is possible to reduce risks due to the close-out shipment or close-out production.

Here, also in the fields of industry other than food and beverage production, there are many known industries in which microorganism contamination causes loss. As described above, the microorganism contamination countermeasure selection system 1 according to the present embodiment can be used for selecting countermeasures not only against microorganism contamination in foods and beverages, but also against microorganism contamination in products in other commercial fields (for example, pharmaceuticals and cosmetics).

In addition, the microorganism contamination countermeasure selection system 1 according to the present embodiment can also be used for detection of drug-resistant bacteria and selection of countermeasures thereof as applications to the medical field.

In addition, for example, it is known that, in latex production, contamination by microorganisms occur because latex is produced according to an aqueous reaction, and the performance of the product deteriorates as the microorganisms grow.

In addition, in optical products, for example, a lens component whose surface is coated with an organic thin film in order to improve optical properties is produced. It is known that, when contamination by microorganisms occurs in this production process, the microorganisms grow on the surface of the lens, which causes deterioration of the performance.

Appropriate microorganism management is required also in the production of such industrial products, and it is possible to provide an economic benefit by applying the microorganism contamination countermeasure selection system 1 according to the present embodiment.

In addition, currently, in water treatment-related facilities, a treatment using activated sludge is widely performed. Activated sludge is a mixture of various microorganisms and organic substances and the like are decomposed by the metabolic activity of these microorganisms. Wastewater flowing into a water treatment facility does not always contain the same components in the same amounts. Therefore, a countermeasure in which components of inflowing wastewater are analyzed, and microorganisms suitable for decomposing the components are allowed to artificially grow in the activated sludge is used, and thus it is possible to increase the water treatment efficiency.

Also in this case, it is not necessary to strictly identify microorganisms in the activated sludge. The purpose can be achieved by controlling features thereof. Also in monitoring of the microorganisms, the microorganism contamination countermeasure selection system 1 according to the present embodiment can be applied.

Here, as described above, in the microorganism contamination countermeasure selection system 1 according to the present embodiment, as long as a specific nucleotide sequence can be detected, its detection method is arbitrary. Therefore, for example, a microarray may be used, sequence analysis may be performed, or other analysis methods may be used.

In order to perform a simple inspection, for example, a detection method using a microarray can be considered. In addition, for example, probes that exhibit fluorescence according to hybridization can be used.

In this case, the probes corresponding to specific nucleotide sequence information linked to each category are used, and at least one spot is assigned and fixed to one type of specific nucleotide sequence linked to one category.

After hybridization with a nucleic acid solution extracted and fragmented from the collected sample is performed, fluorescence measurement is performed, and it is possible to obtain position information of a spot exhibiting fluorescence.

Specific nucleotide sequence information can be identified from the obtained position information (or a combination of position information), and additionally, a category to which this information belongs can be identified.

When the category is identified, it is possible to obtain information on features linked to the category.

Here, in the above embodiment, the microorganism contamination countermeasure selection system 1 is composed of four devices: the microorganism contamination countermeasure selection device 10, the gene analyzing device 20, the product information input device 30, and the statistical information database server 40, but the present invention is not limited thereto. A configuration in which one device has functions of any two or three devices of the above four devices or functions of all (four) devices may be used. For example, a configuration in which one device has functions of the microorganism contamination countermeasure selection device 10, the gene analyzing device 20, and the product information input device 30 described above may be used. In addition, for example, a configuration in which one device has functions of the microorganism contamination countermeasure selection device 10, and the statistical information database server 40 may be used.

Here, a configuration in which a plurality of functions of any device among devices constituting the above microorganism contamination countermeasure selection system 1 are provided in separate devices may be used. For example, a configuration in which a device including the microorganism index determiner 110 and a device including the contamination countermeasure selector 120 are different from each other may be used.

Here, a configuration in which some of functions or some of data provided in any device among devices constituting the above microorganism contamination countermeasure selection system 1 may be included in another device may be used. For example, a configuration in which the microorganism index determiner 110 includes the gene analyzing device 20 instead of the microorganism contamination countermeasure selection device 10 may be used.

While embodiments of the invention have been described above in detail, the specific configuration is not limited to the above embodiments, and various design changes can be made without departing from the spirit and scope of the invention.

Here, some or all parts of the microorganism contamination countermeasure selection system 1 in the above embodiments may be realized by a computer. In this case, a program for realizing the control function may be recorded in a computer readable recording medium, the program recorded in the recording medium may be read and executed in a computer system for realization.

Here, "computer system" here is a computer system built in the microorganism contamination countermeasure selection system 1 and includes hardware such as an OS and peripheral devices. In addition, "computer readable recording medium" refers to a storage device, for example, a portable medium such as a flexible disk, a magneto-optical disc, a ROM, and a CD-ROM and a hard disk built in a computer system.

In addition, the "computer readable recording medium" may include a medium that dynamically maintains a program for a short time like a communication line when a program is transmitted via a network such as the Internet or a communication line such as a telephone line and a medium that maintains a program for a certain time like a volatile memory in the computer system serving as a server or a client in that case. In addition, the program may be a program for realizing some of the above-described functions and the above-described functions may be realized in a combination with a program already recorded in the computer system.

In addition, the microorganism contamination countermeasure selection system 1 in the above embodiment may be realized by an integrated circuit such as a large scale integration (LSI). The functional blocks of the microorganism contamination countermeasure selection system 1 may be individually implemented as a processor or some or all thereof may be integrally implemented as a processor. In addition, a method of forming an integrated circuit is not limited to an LSI circuit, and this may be realized by a dedicated circuit or a general-purpose processor. In addition, when a technology for forming an integrated circuit that replaces the LSI circuit appears according to the advance of semiconductor technology, an integrated circuit based on the technology may be used.

While embodiments of the present invention have been described above in detail with reference to the drawings, the specific configuration is not limited to the embodiments, but may include design changes and the like without departing from the spirit and scope of the invention.

REFERENCE SIGNS LIST

1 Microorganism contamination countermeasure selection system
10 Microorganism contamination countermeasure selection device
20 Gene analyzing device
30 Product information input device
40 Statistical information database server
50 Communication network
100 Controller
110 Microorganism index determiner
111 Gene information acquirer
112 Index determiner
113 First storage
120 Contamination countermeasure selector
121 Product information acquirer
122 Statistical information acquirer
123 Analyzer
124 Contamination countermeasure selector
125 Second storage
126 Outputter
200 Controller
201 Detector
202 Analyzer
203 Storage
204 Gene information outputter
300 Controller
310 Product information inputter
311 Sample information inputter
312 Production information inputter
313 Raw material information inputter
320 Product information outputter
400 Controller
401 Request receiver
402 Searcher
403 Storage
404 Statistical information outputter
1131 Microorganism index table
1251 Contamination countermeasure table
2031 Gene information list
4031 Production information statistical data
4032 Raw material information statistical data
4033 Past case data
4034 Follow-up countermeasure data

The invention claimed is:

1. A microorganism contamination countermeasure selection device comprising a hardware-processor that implements:

a gene information acquirer configured to acquire gene information indicating nucleotide sequences of microorganisms contained in a sample, the nucleotide sequences being included in a predetermined gene information list;

an index determiner configured to:
search a microorganism index table for the nucleotide sequences indicated by the gene information acquired by the gene information acquirer, microorganism indexes being associated with at least one of the gene information in the microorganism index table, each of the microorganism indexes being data representing a category of the microorganisms;
identify a microorganism index associated with the searched nucleotide sequences; and determine that the identified microorganism index is a microorganism index corresponding to the microorganisms contained in the sample; and a contamination countermeasure selector configured to select at least one of contamination countermeasures corresponding to the microorganism index determined by the index determiner based on the microorganism index determined by the index determiner and a contamination countermeasure table in which a contamination countermeasure against contamination by the microorganisms is associated with at least one of the microorganism indexes.

2. The microorganism contamination countermeasure selection device according to claim 1, further comprising:
a product information acquirer configured to acquire product information on a product from which the sample is collected,
wherein the contamination countermeasure selector selects the contamination countermeasure based on the product information.

3. The microorganism contamination countermeasure selection device according to claim 2,
wherein the product information comprises at least one of a type of the product, a production time of the product, a sterilization treatment performed on the product and raw materials of the product.

4. The microorganism contamination countermeasure selection device according to claim 2, further comprising:
a statistical information acquirer configured to acquire statistical information comprising at least one of product information used in past contamination countermeasure selection and past contamination countermeasure implementation cases,
wherein the contamination countermeasure selector selects the contamination countermeasure based on the statistical information.

5. The microorganism contamination countermeasure selection device according to claim 1, further comprising:
a first storage medium storing the microorganism index table in which at least one of the gene information is associated with the microorganism indexes; and
a second storage medium storing the contamination countermeasure table in which the microorganism indexes are associated with the contamination countermeasure against contamination by the microorganisms.

6. A microorganism contamination countermeasure selection system comprising a hardware-processor that implements:
a gene analyzer configured to generate gene information based on analysis results of genes of microorganisms contained in a sample, the gene information indicating nucleotide sequences of the microorganisms contained in the sample, the nucleotide sequences being included in a predetermined gene information list;
an index determiner configured to:
search a microorganism index table for the nucleotide sequences indicated by the gene information generated by the gene analyzer, microorganism indexes being associated with at least one of the gene information in the microorganism index table, each of the microorganism indexes being data representing a category of the microorganisms;
identify a microorganism index associated with the searched nucleotide sequences; and
determine that the identified microorganism index is a microorganism index corresponding to the microorganisms contained in the sample; and a contamination countermeasure selector configured to select at least one of contamination countermeasures corresponding to the microorganism index determined by the index determiner based on the microorganism index determined by the index determiner and a contamination countermeasure table in which a contamination countermeasure against contamination by the microorganisms is associated with at least one of the microorganism indexes.

7. The microorganism contamination countermeasure selection system according to claim 6, further comprising:
a product information inputter configured to receive an input of product information on a product from which the sample is collected,
wherein the contamination countermeasure selector selects the contamination countermeasure based on the product information.

8. The microorganism contamination countermeasure selection system according to claim 6, further comprising:
a statistical information storage configured to store statistical information including at least one of product information used in past contamination countermeasure selection and past contamination countermeasure implementation cases, and
wherein the contamination countermeasure selector selects the contamination countermeasure based on the statistical information.

9. The microorganism contamination countermeasure selection system according to claim 6, further comprising:
a first storage medium storing the microorganism index table in which at least one of the gene information is associated with the microorganism indexes; and
a second storage medium storing the contamination countermeasure table in which the microorganism indexes are associated with the contamination countermeasure against contamination by the microorganisms,
wherein the gene analyzer comprises:
a detection device that detects the nucleotide sequence of microorganisms from the microorganisms contained in the sample; and
an information processing device that analyzes the detected nucleotide sequence.

10. A microorganism contamination countermeasure selection method performed by a computer, the microorganism contamination countermeasure selection method comprising:
a gene information acquisition step in which gene information indicating nucleotide sequences of microorganisms contained in a sample is acquired, the nucleotide sequences being included in a predetermined gene information list;
a search step of searching a microorganism index table for the nucleotide sequences indicated by the gene information acquired in the gene information acquisition step, microorganism indexes being associated with at least one of the gene information in the microorganism index table, each of the microorganism indexes being data representing a category of the microorganisms;
an identification step of identifying a microorganism index associated with the searched nucleotide sequences;
an index determination step of determining that the identified microorganism index is a microorganism index corresponding to the microorganisms contained in the sample; and a contamination countermeasure selection step in which at least one of contamination countermeasures corresponding to the microorganism index determined in the index determination step is selected based on the microorganism index determined in the index determination step and a contamination countermeasure table in which a contamination countermeasure against contamination by the microorganisms is associated with at least one of the microorganism indexes.

11. A non-transitory computer readable storage medium storing a microorganism contamination countermeasure selection program causing a computer to execute:

a gene information acquisition step in which gene information indicating nucleotide sequences of microorganisms contained in a sample is acquired, the nucleotide sequences being included in a predetermined gene information list;

a search step of searching a microorganism index table for the nucleotide sequences indicated by the gene information acquired in the gene information acquisition step, microorganism indexes being associated with at least one of the gene information in the microorganism index table, each of the microorganism indexes being data representing a category of the microorganisms;

an identification step of identifying a microorganism index associated with the searched nucleotide sequences;

an index determination step of determining that the identified microorganism index is a microorganism index corresponding to the microorganisms contained in the sample; and a contamination countermeasure selection step in which at least one of contamination countermeasures corresponding to the microorganism index determined in the index determination step is selected based on the microorganism index determined in the index determination step and a contamination countermeasure table in which a contamination countermeasure against contamination by the microorganisms is associated with at least one of the microorganism indexes.

* * * * *